US012697041B2

(12) United States Patent
Isla Garcia

(10) Patent No.: US 12,697,041 B2
(45) Date of Patent: Aug. 4, 2026

(54) SYSTEM FOR DETECTING CATHETER LOOPING OR KNOTTING

(71) Applicant: Becton, Dickinson and Company, Franklin Lakes, NJ (US)

(72) Inventor: Julio Agustin Isla Garcia, Irvine, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 730 days.

(21) Appl. No.: 18/050,407

(22) Filed: Oct. 27, 2022

(65) Prior Publication Data

US 2023/0095164 A1     Mar. 30, 2023

Related U.S. Application Data

(63) Continuation of application No. PCT/US2021/029670, filed on Apr. 28, 2021.

(60) Provisional application No. 63/017,449, filed on Apr. 29, 2020.

(51) Int. Cl.
| | |
|---|---|
| *A61B 5/06* | (2006.01) |
| *A61B 5/00* | (2006.01) |
| *A61B 5/0215* | (2006.01) |
| *G01D 5/20* | (2006.01) |

(52) U.S. Cl.
CPC ............ *A61B 5/062* (2013.01); *A61B 5/0215* (2013.01); *A61B 5/063* (2013.01); *A61B 5/6852* (2013.01); *G01D 5/2066* (2013.01); *A61B 2562/0247* (2013.01)

(58) Field of Classification Search
CPC ....... A61B 5/062; A61B 5/0215; A61B 5/063; A61B 5/6852; A61B 2562/0247; G01D 5/2066
See application file for complete search history.

(56) References Cited

U.S. PATENT DOCUMENTS

| | | |
|---|---|---|
| 3,995,623 A | 12/1976 | Blake et al. |
| 5,645,065 A | 7/1997 | Shapiro et al. |
| 6,076,007 A | 6/2000 | England et al. |
| 6,366,799 B1 | 4/2002 | Acker et al. |
| (Continued) | | |

OTHER PUBLICATIONS

International Search Report and Written Opinion for PCT Application No. PCT/US2021/029670, dated Jul. 15, 2021, 10 pages.

(Continued)

*Primary Examiner* — Sean A Frith
(74) *Attorney, Agent, or Firm* — Kinney & Lange, P.A.

(57) ABSTRACT

A detection system for detecting a loop and/or a knot in a catheter includes a first coil and a second coil in spaced positions on a catheter body of the catheter. A driver is coupled by a wired communication link to the first coil, wherein the driver is configured to transmit a first signal to the first coil. A receiver is coupled by a wired communication link to the second coil, wherein the receiver is configured to receive a second signal from the second coil indicative of a proximity of the first coil and the second coil. A signal analyzer is coupled by a wired or wireless communication link to the receiver that is configured to receive the second signal from the receiver and determine whether there is a change in the second signal indicative of a formation of the loop and/or the knot in the catheter.

21 Claims, 11 Drawing Sheets

(56)                References Cited

U.S. PATENT DOCUMENTS

| | | | |
|---|---|---|---|
| 6,493,573 | B1 | 12/2002 | Martinelli et al. |
| 7,697,972 | B2 | 4/2010 | Verard et al. |
| 8,391,953 | B2 | 3/2013 | Govari et al. |
| 8,403,829 | B2 | 3/2013 | Hirakawa |
| 9,861,338 | B2 | 1/2018 | Kanade et al. |
| 10,346,976 | B2 | 7/2019 | Averbuch et al. |
| 2004/0152974 | A1* | 8/2004 | Solomon ................ A61B 34/20 600/509 |
| 2006/0009754 | A1 | 1/2006 | Boese et al. |
| 2007/0016006 | A1* | 1/2007 | Shachar ............... A61B 5/0507 600/407 |
| 2007/0232898 | A1 | 10/2007 | Huynh et al. |
| 2009/0036769 | A1* | 2/2009 | Zdeblick ............. A61B 5/6851 600/424 |
| 2012/0130228 | A1* | 5/2012 | Zellers ................... A61B 5/062 600/424 |
| 2016/0022292 | A1* | 1/2016 | Stigall ..................... A61F 2/013 606/113 |
| 2016/0278852 | A1* | 9/2016 | Sliwa ................ A61B 18/1492 |
| 2017/0000381 | A1* | 1/2017 | Hauck ............... A61M 25/0127 |
| 2017/0347896 | A1* | 12/2017 | Keyes ................... A61B 5/027 |
| 2019/0239723 | A1 | 8/2019 | Duindam et al. |
| 2019/0298983 | A1* | 10/2019 | Jaroch ................... A61M 5/007 |
| 2019/0365278 | A1* | 12/2019 | Ludwin ................. A61B 5/062 |
| 2022/0039683 | A1* | 2/2022 | Harmer ................. A61B 5/742 |

OTHER PUBLICATIONS

International Preliminary Report on Patentability for PCT Application No. PCT/US2021/029670, dated Nov. 10, 2022, 7 pages.

Zhou, Lindsay, et al. "Transjugular retrieval of a knotted peripherally inserted central venous catheter (Epicutaneo-Cava catheter) in a neonate." BJRI case reports (2016): 20150327.

L'Acqua, Camilla, et al. "Troubles after Swan-Ganz catheter placement in cardiac surgery." Seminars in cardiothoracic and vascular anesthesia. vol. 21. No. 3. Sage CA: Los Angeles, CA: Sage Publications, 2017.

Hillenbrand, Claudia M., et al. "Active device tracking and high-resolution intravascular MRI using a novel catheter- based, opposed-solenoid phased array coil." Magnetic Resonance in Medicine: An Official Journal of the International Society for Magnetic Resonance in Medicine 51.4 (2004): 668-675.

* cited by examiner

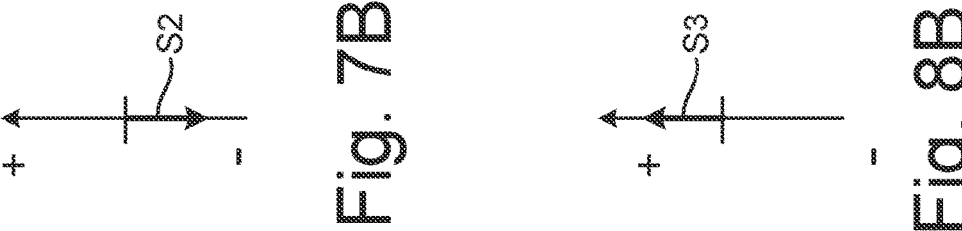
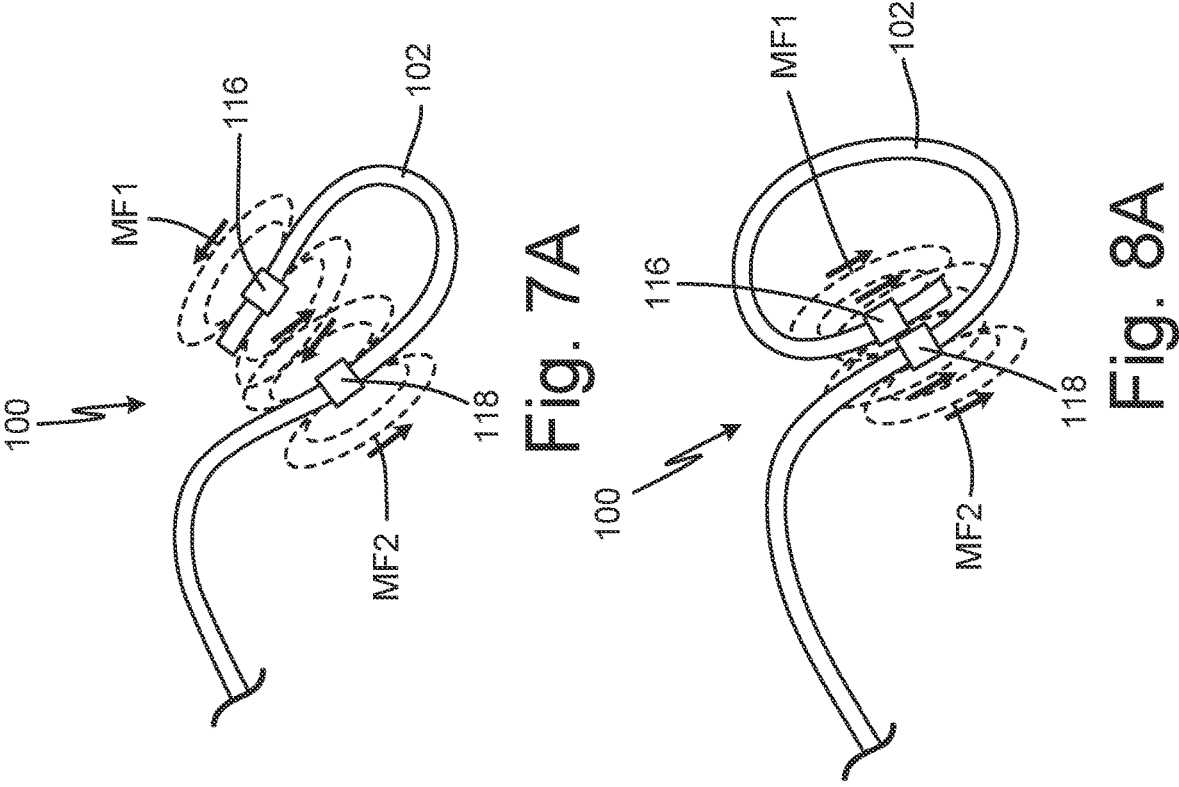

SYSTEM FOR DETECTING CATHETER LOOPING OR KNOTTING

CROSS REFERENCE

This application claims the benefit of PCT/US2021/029670 filed on Apr. 28, 2021, which claims the benefit of U.S. App. No. 63/017,449 filed on Apr. 29, 2020, the entireties of which are each incorporated by reference.

BACKGROUND

The present disclosure relates to pulmonary artery catheters, and in particular, to a system for detecting catheter looping and knotting.

Pulmonary artery catheters, also known as Swan-Ganz catheters, can be advanced into the pulmonary artery of a patient to continuously monitor hemodynamic variables. Pulmonary artery catheters allow for the continuous sensing of flow, pressure, and oxygenation delivery and consumption. Specifically, pulmonary artery catheters can be used to determine the following hemodynamic variables: cardiac output (the volume of blood being pumped by the heart per unit of time), mixed venous oxygen saturation (measure of the relationship between oxygen delivery and oxygen consumption), stroke volume (the volume of blood ejected from the ventricle in each beat), systemic vascular resistance (the resistance that must be overcome to push blood through the circulatory system), right ventricular ejection fraction (the percentage of blood ejected from the ventricle with each beat), right ventricular end diastolic volume (the volume of blood in the ventricle at the end of the diastole), right atrial pressure (the blood pressure in the right atrium of the heart), pulmonary artery pressure (the blood pressure in the pulmonary artery), pulmonary artery occlusion pressure (an estimate of the blood pressure in the left atrium) (also known as the pulmonary wedge pressure), and diastolic pulmonary artery pressure (the blood pressure in the pulmonary artery at the end of the diastole).

The hemodynamic variables that are determined with pulmonary artery catheters can help in the diagnosis, monitoring, and treatment of the following: acute heart failure, severe hypovolemia, complex circulatory situations, medical emergencies, acute respiratory distress syndrome, gram negative sepsis, drug intoxication, acute renal failure, hemorrhagic pancreatitis, intra and post-operative management of high risk patients, history of pulmonary or cardiac disease, fluid shifts, management of high-risk obstetrical patients, diagnosed cardiac disease, toxemia, premature separation of placenta, cardiac output determinations, differential diagnosis of mitral regurgitation and ventricular septal rupture, and diagnosis of cardiac tamponade. Pulmonary artery catheters can also be used to monitor hemodynamic variables during the following procedures: coronary artery bypass graft, aortic valve replacement/repair, mitral valve replacement/repair, aortic valve conduit, aortic arch replacement, cardiogenic shock, acute mitral regurgitation, ventricular septal rupture, and pulmonary artery hypertension.

Pulmonary artery catheters are advanced to a patient's right atrium and an inflatable balloon at a distal end of the pulmonary artery catheter is inflated in the right atrium. The inflatable balloon then floats through the patient's right atrium and right ventricle and will wedge in the pulmonary artery. One of the risks associated with advancing a catheter into the pulmonary artery is looping and knotting of the catheter inside the body. Patients with low blood flow are more susceptible to knotting of the catheter because the catheter is less able to follow the expected trajectory of blood flow through the right atrium and right ventricle into the pulmonary artery. When the catheter does not follow the expected trajectory, it can start coiling and forming one or more loops (most likely in the right atrium or right ventricle of the patient). Eventually, knotting can occur when the catheter is pulled. When knotting does occur, a procedure is needed to undo the knot or surgically remove the catheter from the patient.

SUMMARY

A detection system for detecting a loop and/or a knot in a catheter includes a first coil and a second coil in spaced positions on a catheter body of the catheter. A driver is coupled by a wired communication link to the first coil, wherein the driver is configured to transmit a first signal to the first coil. A receiver is coupled by a wired communication link to the second coil, wherein the receiver is configured to receive a second signal from the second coil indicative of a proximity of the first coil and the second coil. A signal analyzer is coupled by a wired or wireless communication link to the receiver that is configured to receive the second signal from the receiver and determine whether there is a change in the second signal indicative of a formation of the loop and/or the knot in the catheter.

A method for detecting a loop and/or a knot in a catheter includes sending a first signal from a driver to a first coil on the catheter and receiving a second signal from a second coil on a catheter in a receiver. The first coil and the second coil are in spaced positions on a catheter body of the catheter, and the second signal is indicative of a proximity of the first coil and the second coil. The second signal is transmitted from the receiver to a signal analyzer that is coupled to the receiver by a wired or wireless communication link. The signal analyzer determines if there is a change in the second signal that indicates the formation of the loop and/or the knot in the catheter.

BRIEF DESCRIPTION OF THE DRAWINGS

FIG. 7A is a schematic view of the coils on the pulmonary artery catheter when the pulmonary artery catheter starts to loop.

FIG. 7B is a graph showing an amplitude and polarity of a signal when the pulmonary artery catheter starts to loop.

FIG. 8A is a schematic view of the coils on the pulmonary artery catheter when the pulmonary artery catheter has formed a loop.

FIG. 8B is a graph showing an amplitude and polarity of a signal when the pulmonary artery catheter has formed a loop.

DETAILED DESCRIPTION

Figure 1A:
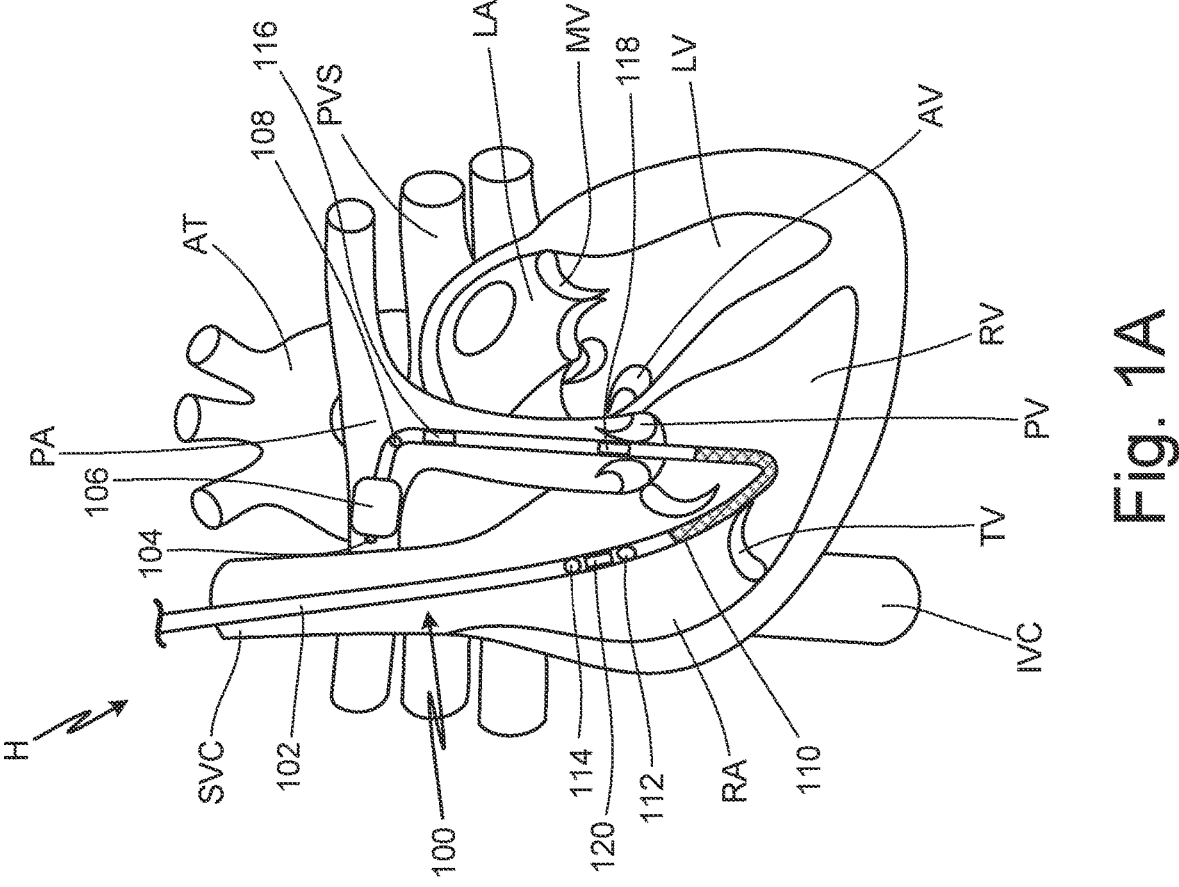
FIG. 1A is a schematic view of a pulmonary artery catheter in a heart.
Figure 1B:
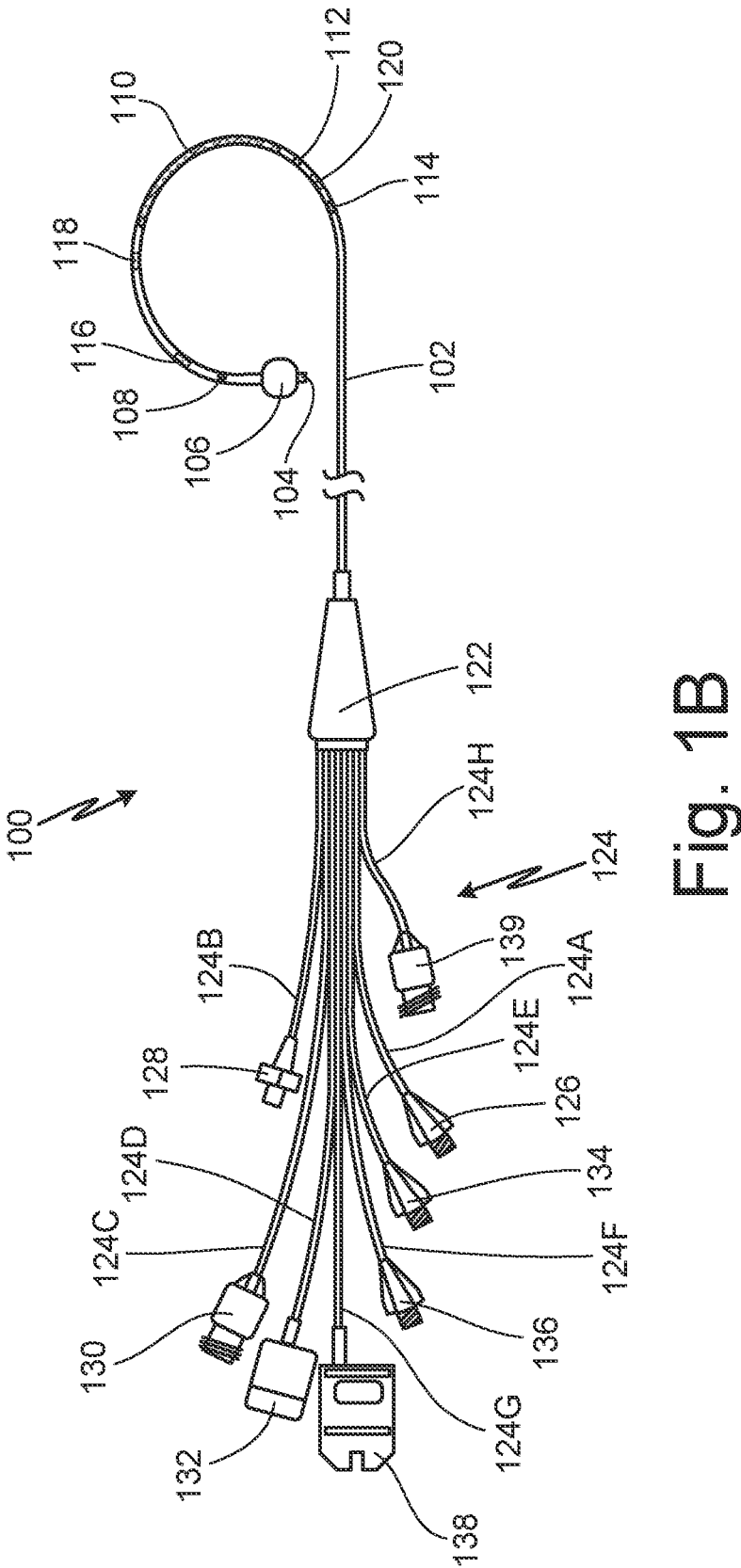
FIG. 1B is a top plan view of the pulmonary artery catheter.

FIG. 1A is a schematic view of pulmonary artery catheter 100 in heart H. FIG. 1B is a top plan view of pulmonary artery catheter 100. Pulmonary artery catheter 100 includes catheter body 102, distal port 104, inflatable balloon 106, thermistor 108, thermal filament 110, proximal injectate port 112, volume infusion port 114, first coil 116, second coil 118, third coil 120, catheter body junction 122 (shown in FIG. 1B), extension tubes 124 (including extension tubes 124A-124H) (shown in FIG. 1B), distal port hub 126 (shown in FIG. 1B), balloon inflation valve 128 (shown in FIG. 1B), thermistor connector 130 (shown in FIG. 1B), thermal filament connector 132 (shown in FIG. 1B), proximal injectate lumen hub 134 (shown in FIG. 1B), volume infusion port hub 136 (shown in FIG. 1B), optical module connector 138 (shown in FIG. 1B), and coil connector 139 (shown in FIG. 1B). FIG. 1A also shows heart H, right atrium RA, right ventricle RV, left atrium LA, left ventricle LV, tricuspid valve TV, pulmonary valve PV, mitral valve MV, aortic valve AV, superior vena cava SVC, inferior vena cava IVC, pulmonary artery PA, pulmonary veins PVS, and aorta AT.

Pulmonary artery catheter 100 (also called a Swan-Ganz catheter) can be advanced to a patient's pulmonary artery PA for continuous monitoring of flow, pressure, and oxygen delivery and consumption. When paired with a cardiac output monitor, pulmonary artery catheter 100 can provide a comprehensive hemodynamic profile of a patient. A patient's hemodynamic status can be tracked using the comprehensive hemodynamic profile and continuous data to assist physicians in early evaluation of the patient's cardiac status. Specifically, pulmonary artery catheter 100 can be used to determine the following parameters when paired with a cardiac monitor: cardiac output (CO), mixed venous oxygen situation (SvO$_2$), stroke volume (SV), systemic vascular resistance (SVR), right ventricular ejection fraction (RVEF), right ventricular end diastolic volume (RVEDV), right atrial pressure (RAP), pulmonary artery pressure (PAP), pulmonary artery occlusion pressure (PAOP), and diastolic pulmonary artery pressure (PADP).

Pulmonary artery catheter 100 includes catheter body 102. Distal port 104 is positioned at a distal end of catheter body 102. Distal port 104 can be used to monitor the pulmonary artery pressure and allows mixed venous blood samples to be taken from pulmonary artery PA for the assessment of oxygen transport balance and the calculation of oxygen consumption, oxygen utilization coefficient, and intrapulmonary shunt fraction. Inflatable balloon 106 is positioned adjacent to distal port 104 near the distal end of catheter body 102. Inflatable balloon 106 can be inflated when pulmonary artery catheter 100 is positioned in heart H and floated into pulmonary artery PA to sense a patient's hemodynamic variables.

Pulmonary artery catheter 100 further includes thermistor 108 positioned proximal of inflatable balloon 106. Thermistor 108 senses a temperature of pulmonary artery PA when inflatable balloon 106 is positioned in pulmonary artery PA. The temperature readings are used to calculate cardiac output measurements. Thermal filament 110 is positioned proximal of thermistor 108. When inflatable balloon 106 is positioned in pulmonary artery PA, thermal filament 110 is positioned in right atrium RA and right ventricle RV of heart H. Proximal injectate port 112 is positioned proximal of thermal filament 110. When inflatable balloon 106 is positioned in pulmonary artery PA, proximal injectate port 112 is positioned in right atrium RA of heart H. Proximal injectate port 112 can be used to determine a right atrial or central venous pressure, to take blood samples, to infuse medicine to right atrium RA, or to inject a fluid bolus into heart H for cardiac output measurement. Volume infusion port 114 is positioned proximal of proximal injectate port 112. When inflatable balloon 106 is positioned in pulmonary artery PA of heart H, volume infusion port 114 is positioned in right atrium RA of heart H. Volume infusion port 114 provides direct access to right atrium RA and allows for continuous infusion into right atrium RA of heart H. In alternate embodiments, pulmonary artery catheter 100 can include electrodes for right atrial, right ventricular, or right A-V sequential temporary transvenous pacing.

First coil 116, second coil 118, and third coil 120 are positioned on catheter body 102 of pulmonary artery catheter 100. In the embodiment shown in FIGS. 1A-1B, first coil 116 is positioned between thermistor 108 and second coil 118, second coil 118 is positioned between first coil 116 and thermal filament 110, and third coil 120 is positioned between proximal injectate port 112 and volume infusion port 114. In alternate embodiments, first coil 116, second coil 118, and third coil 120 can be positioned at any location along catheter body 102. Further, in alternate embodiments, pulmonary artery catheter 100 can include two coils or four or more coils.

Catheter body junction 122 is positioned at a proximal end of catheter body 102. Extending from catheter body junction 122 are plurality of extension tubes 124. There are eight extension tubes 124 shown in FIG. 1B, but any number of extension tubes 124 can extend from catheter body junction 122 in alternate embodiments. Each of extension tubes 124 extends from catheter body junction 122 to a connector at a proximal end of each extension tube 124.

Distal port hub 126 is positioned at a proximal end of extension tube 124A. Distal port hub 126 is fluidly connected to distal port 104 through a lumen extending through catheter body 102 and through extension tube 124A. Balloon inflation valve 128 is positioned at a proximal end of extension tube 124B. Balloon inflation valve 128 is fluidly connected to inflatable balloon 106 through a lumen extending through catheter body 102 and through extension tube 124B. An injection device, such as a syringe, can be connected to balloon inflation valve 128 to inject a fluid into inflatable balloon 106.

Thermistor connector 130 is positioned at a proximal end of extension tube 124C. Thermal filament connector 132 is positioned at a proximal end of extension tube 124D.

Proximal injectate lumen hub 134 is positioned at a proximal end of extension tube 124E. Proximal injectate lumen hub 134 is fluidly connected to proximal injectate port 112 through a lumen extending through catheter body 102 and through extension tube 124E. Volume infusion port hub 136 is positioned at a proximal end of extension tube 124F. Volume infusion port hub 136 is fluidly connected to volume infusion port 114 through a lumen extending through catheter body 102 and through extension tube 124F. Optical module connector 138 is positioned at a proximal end of extension tube 124G.

Coil connector 139 is positioned at a proximal end of extension tube 124H. Coil connector 139 is coupled by a wired communication link to first coil 116, second coil 118, and third coil 120. Coil connector 139 is configured to be coupled by a wired communication link to a detection system for detecting loops or knots that may form in catheter body 102 of pulmonary artery catheter 100. Coil connector 139 thus couples the detection system to first coil 116, second coil 118, and third coil 120.

Pulmonary artery catheter 100 can be inserted into a large vein in the patient, typically the internal jugular veins, the subclavian veins, the femoral veins, or the antecubital fossa veins. Pulmonary artery catheter 100 is then advanced through the vascular systems and into the right atrium RA of heart H. The passage of pulmonary artery catheter 100 to the right atrium RA can be monitored with dynamic pressure readings from distal port 104 on pulmonary artery catheter 100 and/or with fluoroscopy. Once the distal end of pulmonary artery catheter 100 is positioned in right atrium RA of heart H, inflatable balloon 106 is inflated. Inflatable balloon 106 will then float from right atrium RA, through tricuspid valve TV, into and through right ventricle RV, through pulmonary valve PV, and into pulmonary artery PA. Inflatable balloon 106 will float through pulmonary artery PA until it wedges in pulmonary artery PA, as shown in FIG. 1A.

Pulmonary artery catheter 100 can determine hemodynamic parameters as inflatable balloon 106 is floated through heart H. Once inflatable balloon 106 is wedged in pulmonary artery PA, pulmonary artery catheter 100 can determine further hemodynamic parameters. Once the hemodynamic parameters are determined, inflatable balloon 106 can be deflated and pulmonary artery catheter 100 can be pulled from the patient.

One of the risks associated with advancing pulmonary artery catheter 100 into pulmonary artery PA is that pulmonary artery catheter 100 can form a loop or knot. Patients with low blood flow are more susceptible to knotting of pulmonary artery catheter 100 because pulmonary artery catheter 100 is less able to follow the expected trajectory of blood flow through right atrium RA and right ventricle RV into pulmonary artery PA. When pulmonary artery catheter 100 does not follow the expected trajectory, it can start coiling and forming one or more loops (most likely in right atrium RA or right ventricle RV of the patient). Eventually, knotting can occur when pulmonary artery catheter 100 is pulled. When knotting does occur, a procedure is needed to undo the knot or surgically remove pulmonary artery catheter 100 from the patient.

First coil 116, second coil 118, and third coil 120 are configured to be coupled to a detection system to detect looping or knotting of catheter body 102 of pulmonary artery catheter 100. The detection system is described with respect to FIGS. 2-13B.

Figure 2:
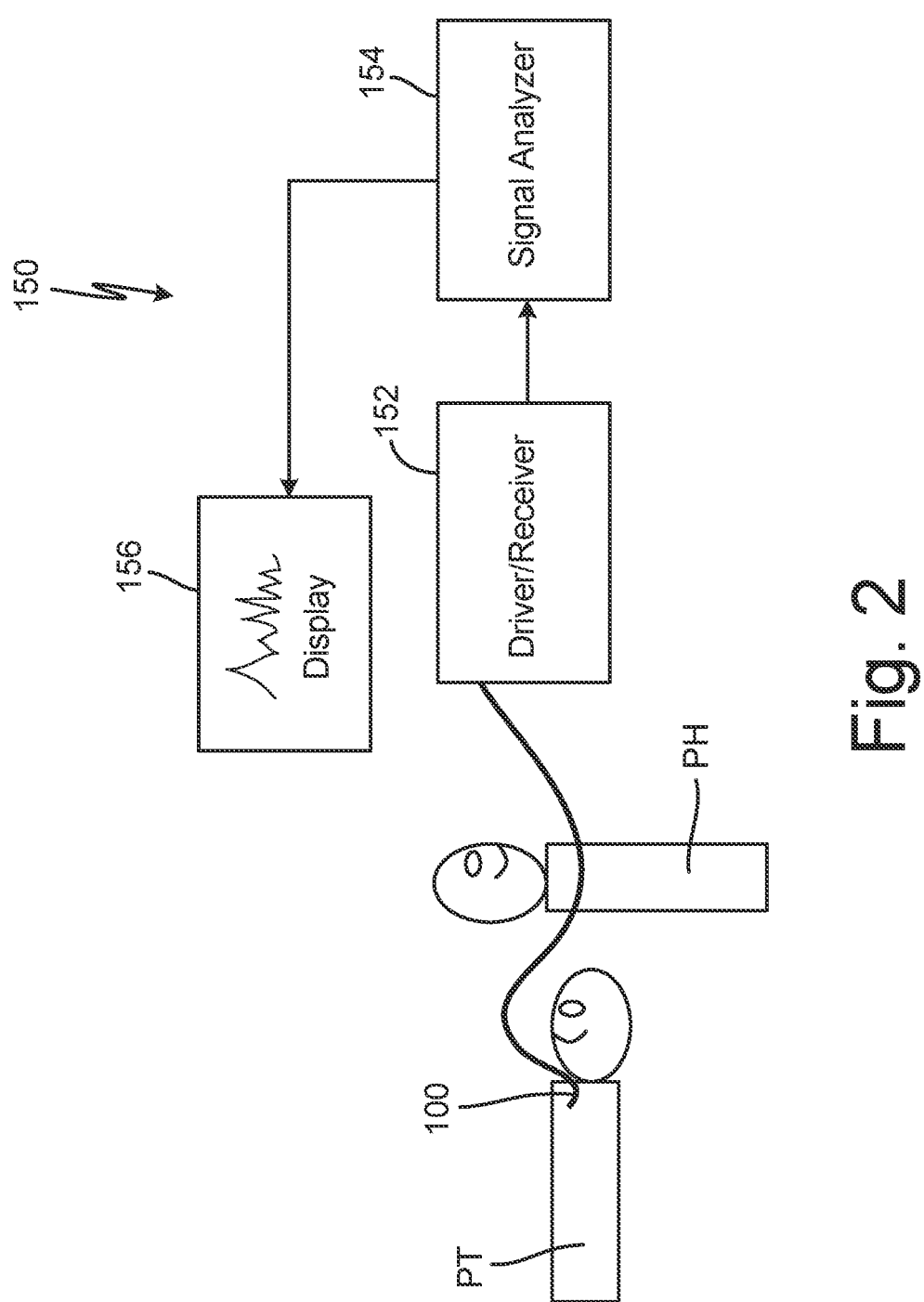
FIG. 2 is a schematic view of a first embodiment of a detection system for detecting looping and knotting of a pulmonary artery catheter.
Figure 3:
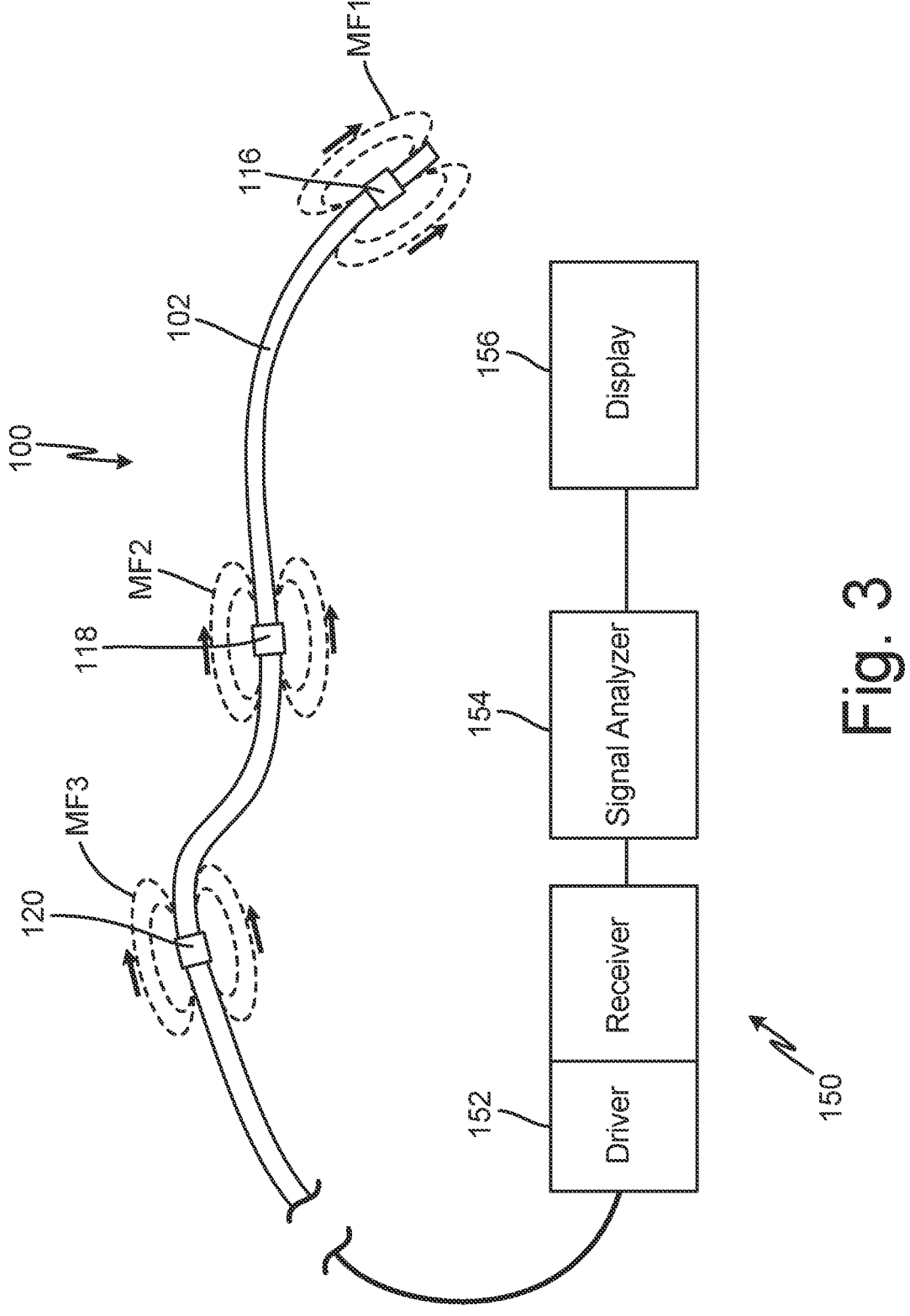
FIG. 3 is a schematic view of the first embodiment of the detection system including coils on a pulmonary artery catheter.

FIG. 2 is a schematic view of detection system 150 for detecting looping and knotting of pulmonary artery catheter 100. FIG. 3 is a schematic view of detection system 150 including coils on pulmonary artery catheter 100. FIGS. 2-3 will be discussed together. FIGS. 2-3 show pulmonary artery catheter 100 and detection system 150. Catheter 100 includes catheter body 102 (shown in FIG. 3), first coil 116 (shown in FIG. 3), second coil 118 (shown in FIG. 3), and third coil 120 (shown in FIG. 3). Detection system 150 includes driver/receiver 152, signal analyzer 154, and display 156. FIG. 2 also shows patient PT and physician PH. FIG. 3 also shows first magnetic field MF1, second magnetic field MF2, and third magnetic field MF3.

Catheter 100 is schematically shown in FIGS. 2-3, but it has the structure and design as shown in and discussed in reference to FIGS. 1A-1B. Catheter 100 includes catheter body 102 with first coil 116, second coil 118, and third coil 120 positioned on catheter body 102. Detection system 150 will be discussed here as detecting looping and knotting of catheter 100, but detection system 150 can be used with any suitable catheter to prevent looping and knotting of any suitable catheter in alternate embodiments.

Detection system 150 is used to detect looping or knotting of catheter body 102 of catheter 100. First coil 116, second coil 118, and third coil 120 are positioned in spaced positions on catheter body 102 and form a part of detection system 150. In the embodiment shown in FIGS. 1A-1B and 3, catheter 100 includes three coils, including first coil 116, second coil 118, and third coil 120. In alternate embodiments, detection system 150 can include two coils or four or more coils. The more coils that are positioned along catheter body 102 can increase the accuracy of detection system 150. In the embodiment shown in FIG. 3, first coil 116, second coil 118, and third coil 120 are positioned in spaced positions on a distal portion of catheter body 102 of catheter 100. The distal portion is the portion of catheter body 102 that is positioned in a heart and a pulmonary artery of patient PT when catheter 100 is fully positioned in patient PT. First coil 116 is positioned between a distal end of catheter 100 and second coil 118; second coil 118 is positioned between first coil 116 and third coil 120; and third coil 120 is positioned between second coil 118 and a proximal end of catheter 100.

As shown in FIG. 2, physician PH can insert catheter 100 into patient PT. Catheter 100 extends out of patient PT and a proximal end of catheter 100 is connected to driver/receiver 152 with coil connector 139 (shown in FIGS. 1A-1B). First coil 116, second coil 118, and third coil 120 are electrically coupled to driver/receiver 152 by one or more wired communication links. Driver/receiver 152 is configured to send a signal to first coil 116, second coil 118, and/or third coil 120 and to receive a signal from first coil 116, second coil 118, and/or third coil 120 in return. Driver/receiver 152 is electrically coupled to signal analyzer 154 by a wired or wireless communication link. The signal received in driver/receiver 152 from first coil 116, second coil 118, and/or third coil 120 can be communicated to signal analyzer 154 from driver/receiver 152. Signal analyzer 154 is configured to analyze the signal.

In the embodiment shown in FIGS. 2-3, driver/receiver 152 is a single unit. In alternate embodiments, driver/receiver 152 can be two separate components. Driver/receiver 152 drives first coil 116, second coil 118, and/or third coil 120 with an AC signal. Driver/receiver 152 can generate an AC current and detect an AC voltage in some embodiments, and driver/receiver 152 can generate an AC voltage and detect an AC current in alternate embodiments. When the AC signal is transmitted to first coil 116, second coil 118, and/or third coil 120 from driver/receiver 152, a magnetic field is created around each of first coil 116, second coil 118, and/or third coil 120. As shown in FIG. 3, first magnetic field MF1 is formed around first coil 116, second magnetic field MF2 is formed around second coil 118, and third magnetic field MF3 is formed around third coil 120. First magnetic field MF1, second magnetic field MF2, and third magnetic field MF3 are schematically shown in FIG. 3. The polarity of each of first magnetic field MF1, second magnetic field MF2, and third magnetic field MF3 is shown with arrows in FIG. 3. The polarity of each of first magnetic field MF1, second magnetic field MF2, and third magnetic field MF3 are based on the winding and excitation of first coil 116, second coil 118, and third coil 120, respectively, at any given time and the proximity of first coil 116, second coil 118, and third coil 120. A signal from first coil 116, second coil 118, and/or third coil 120 is received in driver/receiver 152. The signal that is received in driver/receiver 152 will be indicative of the proximity of first coil 116, second coil 118, and third coil 120 to one another. When catheter 100 is not looped or knotted, the signal that is received in driver/receiver 152 will correlate to first coil 116, second coil 118, and third coil 120 being in spaced positions on the distal portion of catheter body 102 of catheter 100. If a loop or knot starts to form in catheter body 102 of catheter 100, the signal that is received in driver/receiver 152 will indicate a change that is indicative of first coil 116, second coil 118, and third coil 120 coming into proximity with one another and the formation of the loop and/or the knot in catheter body 102 of catheter 100. To simply the description herewith, the mutual coupling (inductance) of first coil 116, second coil 118, and/or third coil 120 will be ignored hereinafter.

Detection system 150 is configured to detect changes in first magnetic field MF1, second magnetic field MF2, and/or third magnetic field MF3 when a loop or a knot starts to form in catheter 100. Driver/receiver 152 is configured to receive a signal from first coil 116, second coil 118, and/or third coil 120 that is indicative of the proximity of first coil 116, second coil 118, and third coil 120 to one another. The signal received in driver/receiver 152 is then transmitted to signal analyzer 154 and can be analyzed by signal analyzer 154.

In a first embodiment, driver/receiver 152 can be coupled to one or more of first coil 116, second coil 118, and third coil 120 along a first wired communication link and to the remaining of first coil 116, second coil 118, and third coil 120 along a second wired communication link. In this embodiment, driver/receiver 152 will drive the one or more coils (transmit coil(s)) connected to the first wired communication link and receive a signal from the one or more coils (receive coil(s)) connected to the second wired communication link. When the driver/receiver 152 drives the transmit coil(s) connected to the first wired communication link with an AC signal, a magnetic field if created around each of the transmit coil(s). A signal is induced into the receive coil(s) due to the proximity of the coils that is indicative of the proximity of first coil 116, second coil 118, and third coil 120 to one another. If a loop or knot starts to form in catheter body 102 of catheter 100, the signal that is received in driver/receiver 152 will indicate a change that is indicative of first coil 116, second coil 118, and third coil 120 coming into proximity with one another and the formation of the loop and/or the knot in catheter body 102 of catheter 100.

In a second embodiment, driver/receiver 152 can be coupled to first coil 116, second coil 118, and third coil 120 along a single wired communication link. First coil 116, second coil 118, and third coil 120 can be coupled in series or in parallel to the wired communication link. In this embodiment, driver/receiver 152 will drive first coil 116, second coil 118, and third coil 120 and receive a signal from first coil 116, second coil 118, and third coil 120. The signal that is received in driver/receiver 152 will be a function of an impedance of first coil 116, second coil 118, and third coil 120, and the coupling thereof, that is indicative of the proximity of first coil 116, second coil 118, and third coil 120 to one another. If a loop or knot starts to form in catheter body 102 of catheter 100, the signal that is received in driver/receiver 152 will indicate a change in impedance that is indicative of first coil 116, second coil 118, and third coil 120 coming into proximity with one another and the formation of the loop and/or the knot in catheter body 102 of catheter 100.

Changes in the signal from first coil 116, second coil 118, and/or third coil 120 can include changes to the amplitude (or magnitude), polarity (or phase), and/or trend of the signal that indicates changes to first magnetic field MF1, second magnetic field MF2, and/or third magnetic field MF3. Signal analyzer 154 uses an algorithm to compute the likelihood of loop or knot formation based on an analysis of the amplitude, polarity, and/or trend of the signal from first coil 116, second coil 118, and/or third coil 120.

Signal analyzer 154 is electrically coupled to display 156 by a wired or wireless communication link. After the signal from first coil 116, second coil 118, and/or third coil 120 is analyzed by signal analyzer 154, an instruction signal is transmitted from signal analyzer 154 to display 156. Display 156 can be configured to display a representation of the signal from first coil 116, second coil 118, and/or third coil 120, provide an alarm to physician PH regarding looping and/or knotting of catheter 100, and/or instruct physician PH regarding the advancement or removal of catheter 100 when looping and/or knotting of catheter 100 has occurred. For example, the instruction signal that is communicated to display 156 can include an instruction to display an amplitude and a polarity of the signal from first coil 116, second coil 118, and/or third coil 120 on display 156. If signal analyzer 154 has detected a change in the signal from first coil 116, second coil 118, and/or third coil 120 that indicates the formation of a loop and/or a knot in catheter 100, the instruction signal can include an instruction to display 156 to provide an alarm to physician PH. Further, if signal analyzer 154 has detected a change in the signal from first coil 116, second coil 118, and/or third coil 120 that indicates the formation of a loop and/or a knot in catheter 100, the instruction signal can include instructions that are to be provided to physician PH through display 156 regarding the advancement or removal of catheter 100.

Detection system 150 provides a method for real-time, continuous, uninterrupted detection of catheter loop formation and issuance of an alarm if a knot is likely to form. Detection system 150 is suitable for guiding the floating procedure of pulmonary artery catheter 100 to prevent knotting of pulmonary artery catheter 100. Detection system 150 can determine whether a loop or knot is forming in pulmonary artery catheter 100 based on an analysis of signals from first coil 116, second coil 118, and/or third coil 120. Compared to prior art devices, no extra-corporeal sensing devices are required. Further, detection system 150 provides higher immunity to metal bodies that are close to patient PT that can affect first magnetic field MF1, second magnetic field MF2, and third magnetic field MF3 of first coil 116, second coil 118, and third coil 120, respectively, as an extra-corporeal sensing device is not needed. This allows catheter 100 and detection system 150 to be used in clinic or hospital settings around medical equipment utilizing magnetic fields.

Figure 4:
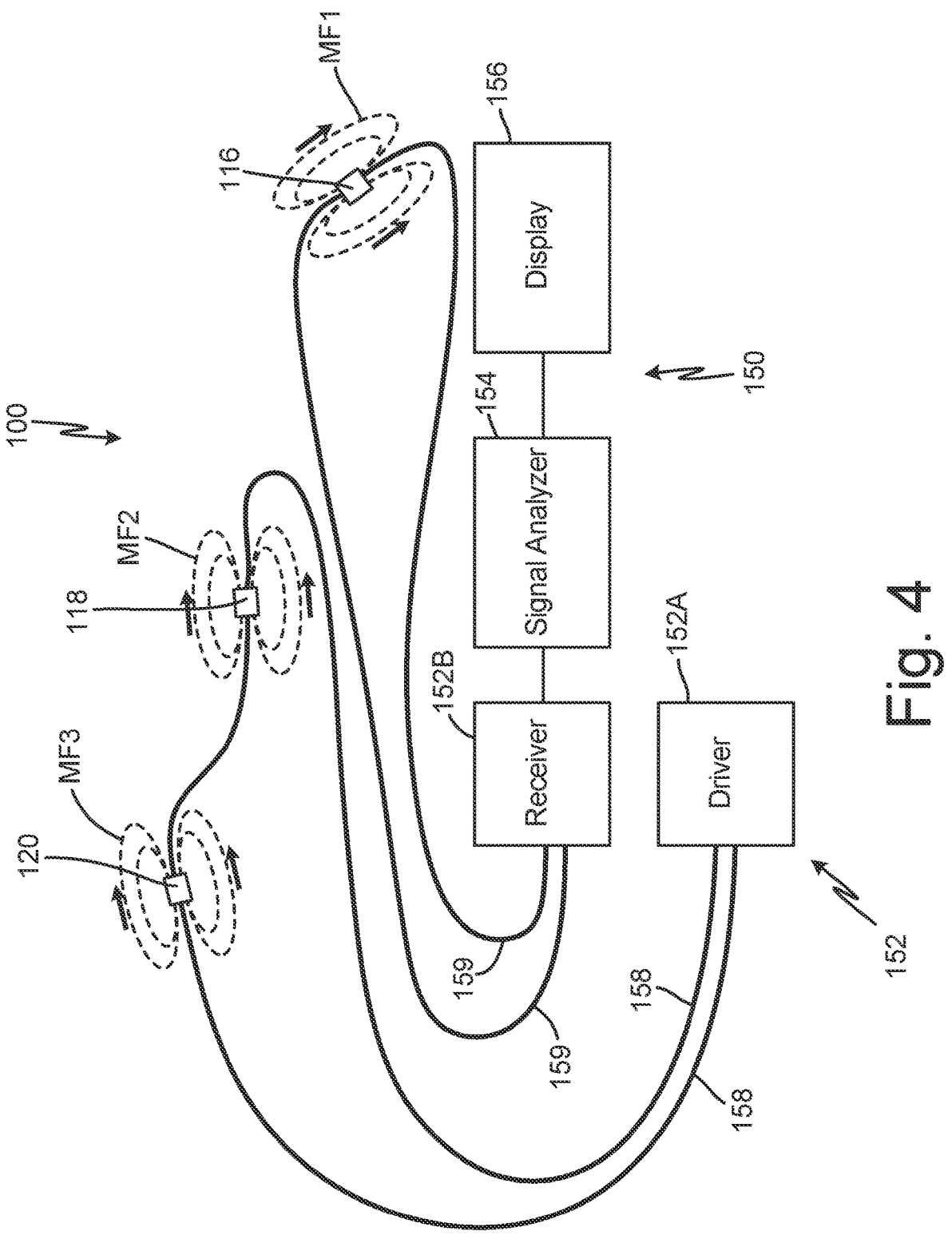
FIG. 4 is a schematic view of a first configuration of the first embodiment of the detection system.

FIG. 4 is a schematic view of a first configuration of detection system 150. FIG. 4 shows first coil 116, second coil 118, third coil 120, and detection system 150, which includes driver/receiver 152 (including driver 152A and receiver 152B), signal analyzer 154, display 156, transmit wires 158, and receive wires 159. FIG. 4 also shows first magnetic field MF1, second magnetic field MF2, and third magnetic field MF3.

Catheter 100 and catheter body 102 are not shown in FIG. 4 for clarity. FIGS. 1A-1B above show the structure and design of catheter 100 and catheter body 102, including the positioning of first coil 116, second coil 118, and third coil 120 in spaced positions on the distal portion of catheter body 102. Detection system 150 will be discussed here as detecting looping and knotting of catheter 100, but detection system 150 can be used with any suitable catheter to prevent looping and knotting of any suitable catheter in alternate embodiments. Detection system 150 is used to detect looping or knotting of catheter body 102 of catheter 100. First coil 116, second coil 118, and third coil 120 are positioned in spaced positions on catheter body 102 and form a part of detection system 150.

Detection system 150 has generally the same structure and design as discussed above with respect to FIGS. 2-3, however driver/receiver 152 includes driver 152A and receiver 152B that are separate components in the configuration of detection system 150 shown in FIG. 4. In the configuration of detection system 150 shown in FIG. 4, second coil 118 and third coil 120 are electrically coupled to driver 152A with transmit wires 158, and first coil 116 is electrically coupled to receiver 152B with receive wires 159. Second coil 118 and third coil 120 are shown as being connected in series in the embodiment shown in FIG. 4, but can also be connected in parallel along transmit wires 158. Driver 152A is configured to send a signal to second coil 118 and third coil 120, and receiver 152B is configured to receive a signal from first coil 116. As such, second coil 118 and third coil 120 are transmit coils and first coil 116 is a receive coil. In alternate embodiments, detection system 150 can include one transmit coil and one receive coil, two or more transmit coils and one receive coil, one transmit coil and two or more receive coils, or two or more transmit coils and two or more receive coils. If two or more receive coils are included, the receive coils can be connected in series or in parallel along receive wires 159. Receiver 152B is electrically coupled to signal analyzer 154 by a wired or wireless communication link. The signal received in receiver 152B from first coil 116 can be communicated to signal analyzer 154 from receiver 152B. Signal analyzer 154 is configured to analyze the signal.

Driver 152A drives second coil 118 and third coil 120 (the transmit coils) with an AC signal. Driver 152A can generate an AC current or an AC voltage. When driven with the AC signal, a magnetic field is created around each of second coil 118 and third coil 120. As shown in FIG. 4, second magnetic field MF2 is formed around second coil 118 and third magnetic field MF3 is formed around third coil 120. The polarity of each of second magnetic field MF2 and third magnetic field MF3 is shown with arrows in FIG. 4. The polarity of each of second magnetic field MF2 and third magnetic field MF3 are based on the winding and excitation of second coil 118 and third coil 120, respectively, at any given time and the proximity of second coil 118 and third coil 120.

A signal is induced into first coil 116 (the receive coil) due to the proximity of first coil 116 to second coil 118 and third coil 120. Magnetic field MF1 is formed around first coil 116.

A signal from first coil 116 (the receive coil) is received in receiver 152B. Receiver 152B can detect an AC voltage or an AC current. The signal that is received in receiver 152B will be indicative of the proximity of first coil 116, second coil 118, and/or third coil 120 to one another. When catheter 100 is not looped or knotted, the signal that is received in receiver 152B will correlate to first coil 116, second coil 118, and third coil 120 being in spaced positions on the distal portion of catheter body 102 of catheter 100. If a loop or knot starts to form in catheter body 102 of catheter 100, the signal that is received in receiver 152B will indicate a change that is indicative of first coil 116, second coil 118, and/or third coil 120 coming into proximity with one another and the formation of the loop and/or the knot in catheter body 102 of catheter 100. Due to the transmit and receive reciprocity, first magnetic field MF1, second magnetic field MF2, and third magnetic field MF3 are also indicative of their spatial sensitivity to externally generated fields.

Detection system 150 is configured to detect changes in first magnetic field MF1 of first coil 116 (the receive coil) when a loop or a knot starts to form in catheter 100. Receiver 152B is configured to receive a signal from first coil 116 that is indicative of the proximity of first coil 116, second coil 118, and third coil 120 to one another. The signal received in receiver 152B is then sent to signal analyzer 154 and can be analyzed by signal analyzer 154. Changes in the signal from first coil 116 (the receive coil) can include changes to the amplitude, polarity, and/or trend of the signal that indicates changes to first magnetic field MF1 of first coil 116. Signal analyzer 154 uses an algorithm to compute the likelihood of loop or knot formation based on an analysis of the amplitude, polarity, and/or trend of the signal from first coil 116.

Signal analyzer 154 is electrically coupled to display 156 by a wired or wireless communication link. After the signal from first coil 116 is analyzed by signal analyzer 154, an instruction signal is communicated from signal analyzer 154 to display 156. Display 156 can be configured to display a representation of the signal from first coil 116, provide an alarm to physician PH regarding looping and/or knotting of catheter 100, and/or instruct physician PH regarding the advancement or removal of catheter 100 when looping and/or knotting of catheter 100 has occurred. For example, the instruction signal that is communicated to display 156 can include an instruction to display an amplitude and a polarity of the signal from first coil 116 on display 156. If signal analyzer 154 has detected a change in the signal from first coil 116 that indicates the formation of a loop and/or a knot in catheter 100, the instruction signal can include an instruction to display 156 to provide an alarm to physician PH. Further, if signal analyzer 154 has detected a change in the signal from first coil 116 that indicates the formation of a loop and/or a knot in catheter 100, the instruction signal can include instructions that are to be provided to physician PH through display 156 regarding the advancement or removal of catheter 100.

Having one or more of first coil 116, second coil 118, and third coil 120 be a transmit coil(s) and one or more of first coil 116, second coil 118, and third coil 120 be a receive coil(s) permits for use of receiver 152B with a lower dynamic range and/or reduces the direct electrical noise coupling between driver 152A and receiver 152B. This allows a lower current or voltage level to be used to drive first coil 116, second coil 118, and/or third coil 120.

Figure 5:
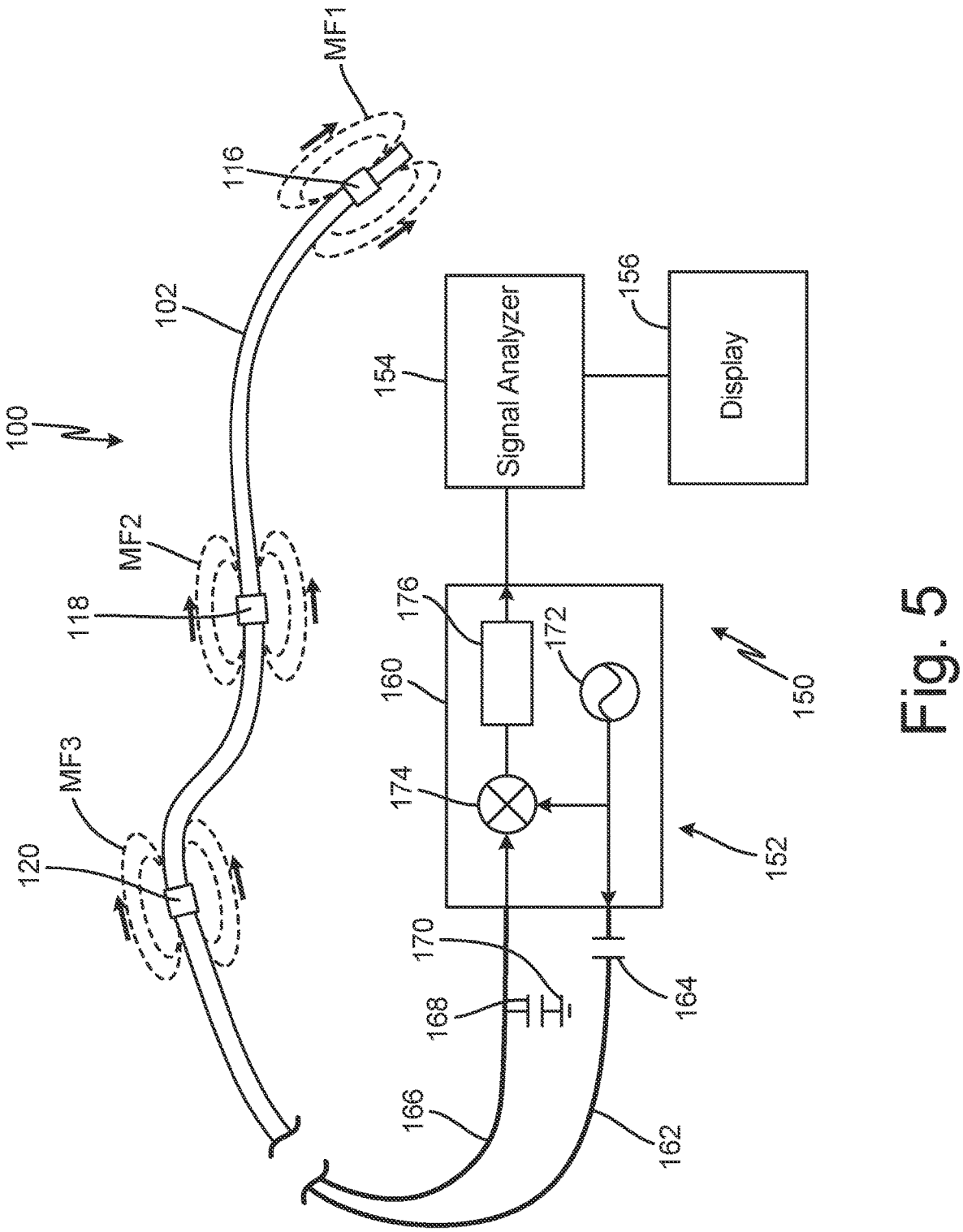
FIG. 5 is a schematic view of the pulmonary artery catheter and the first embodiment of the detection system with a lock-in amplifier.

FIG. 5 is a schematic view of pulmonary artery catheter 100 and detection system 150 with lock-in amplifier 160. Pulmonary artery catheter 100 includes catheter body 102, first coil 116, second coil 118, and third coil 120. Detection system 150 includes driver/receiver 152, signal analyzer 154, display 156, lock-in amplifier 160, transmit wire 162, capacitor 164, receive wire 166, capacitor 168, and ground 170. Lock-in amplifier 160 includes reference source 172, demodulator 174, and low pass filter 176. FIG. 5 also shows first magnetic field MF1, second magnetic field MF2, and third magnetic field MF3.

Catheter 100, catheter body 102, first coil 116, second coil 118, and third coil 120 are schematically shown in FIG. 5, but have the structure and design as shown in and discussed in reference to FIGS. 1A-1B. Detection system 150 will be discussed here as detecting looping and knotting of catheter 100, but detection system 150 can be used with any suitable catheter to prevent looping and knotting of any suitable catheter in alternate embodiments.

Detection system 150 includes driver/receiver 152, signal analyzer 154 and display 156, as discussed above in reference to FIGS. 2-4. Driver/receiver 152 includes lock-in amplifier 160 in the embodiment shown in FIG. 5. Lock-in amplifier 160 is one version of driver/receiver 152 that can be used in detection system 150. Lock-in amplifier 160 is configured to send a signal to and receive a signal from first coil 116, second coil 118, and/or third coil 120. Lock-in amplifier 160 is one example of driver/receiver 152 that can be used to drive first coil 116, second coil 118, and/or third coil 120 and receive signals from first coil 116, second coil 118, and/or third coil 120. In alternate embodiments, any suitable mechanism can be used for driver/receiver 152.

In the embodiment shown in FIG. 5, lock-in amplifier 160 is a multi-channel lock-in amplifier, second coil 118 and third coil 120 are transmit coils, and first coil 116 is a receive coil. Lock-in amplifier 160 sends the signal to second coil 118 and third coil 120 along transmit wire 162 that is electrically coupled to second coil 118 and third coil 120. Transmit wire 162 is shown as being a single wire in the embodiment shown in FIG. 5, but can include a second (return or ground) wire that is not shown for simplicity. Lock-in amplifier 160 sends a sinusoidal signal (AC signal) to second coil 118 and third coil 120 that is preferably between 10 Hertz (Hz) and 100 kiloHertz (kHz). Capacitor 164 is positioned along transmit wire 162 between lock-in amplifier 160 and third coil 120. Capacitor 164 acts as a short circuit for high frequencies and will block DC components. Capacitor 164 is tuned to create series resonance with second coil 118 and third coil 120 to maximize current passing through second coil 118 and third coil 120. The sinusoidal signal drives second coil 118 and third coil 120.

Receive wire 166 will extend from and electrically couple first coil 116 to lock-in amplifier 160. Receive wire 166 is shown as being a single wire in the embodiment shown in FIG. 5, but can include a second (return or ground) wire that is not shown for simplicity. A signal from first coil 116 will be received in lock-in amplifier 160 along receive wire 166. Capacitor 168 and ground 170 are positioned along receive wire 166 between first coil 116 and lock-in amplifier 160. Capacitor 168 and ground 170 will remove high-frequency signals from the signal being received from first coil 116. Capacitor 168 is tuned to create parallel resonance to maximize voltage detected at a frequency of interest.

Lock-in amplifier 160 includes reference source 172, demodulator 174, and low pass filter 176. Reference source 172 generates the sinusoidal signal (AC signal) that is sent to second coil 118 and third coil 120 along transmit wire 162. Reference source 172 also sends the sinusoidal signal (AC signal) to demodulator 174 of lock-in amplifier 160 to act as a reference signal for demodulator 174. Demodulator 174 receives the signal from first coil 116 along receive wire 166. Demodulator 174 uses the reference signal from reference source 172 to demodulate the signal received from first coil 116. Demodulator 174 then sends the signal to low pass filter 176, which filters out AC artifacts. The resulting signal is correlated to the proximity of first coil 116, second coil 118, and third coil 120 to one another.

The resulting signal in lock-in amplifier 160 is then communicated from lock-in amplifier 160 to signal analyzer 154. As discussed above in reference to FIGS. 2-4, signal analyzer 154 analyzes the signal from lock-in amplifier 160 to determine whether there is a change to the amplitude, polarity, or trend of the signal that indicates the formation of a loop and/or a knot in catheter 100. If there is a change indicating the formation of a loop and/or a knot in catheter 100, signal analyzer 154 can provide an instruction signal to display 156 to display the signal, provide an alarm, and instruct a physician on the advancement or removal of catheter 100.

Figures 6A, 6B:
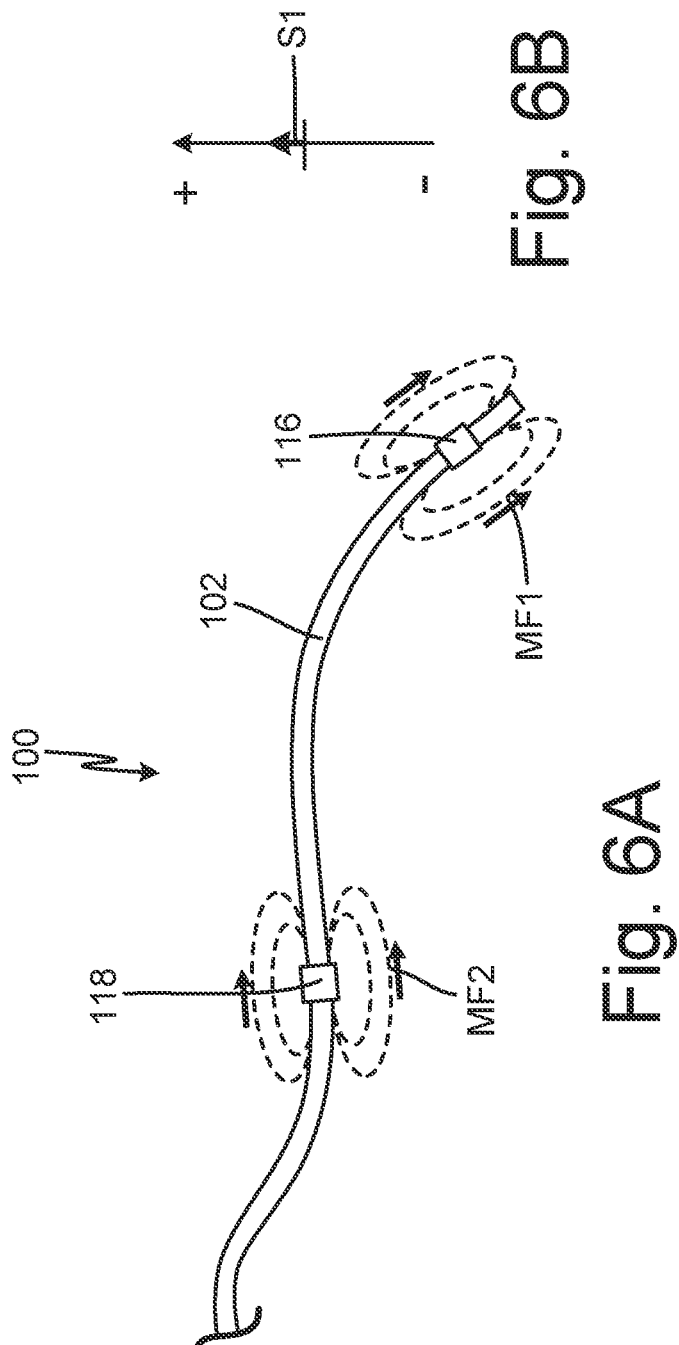
FIG. 6A is a schematic view of coils on the pulmonary artery catheter when the pulmonary artery catheter is not looped or knotted.
FIG. 6B is a graph showing an amplitude and polarity of a signal from the coils when the pulmonary artery catheter is not looped or knotted.

FIG. 6A is a schematic view of coils on pulmonary artery catheter 100 when pulmonary artery catheter 100 is not looped or knotted. FIG. 6B is a graph showing an amplitude and polarity of signal S1 from the coils when pulmonary artery catheter 100 is not looped or knotted. FIG. 7A is a schematic view of the coils on pulmonary artery catheter 100 when pulmonary artery catheter 100 starts to loop. FIG. 7B is a graph showing an amplitude and polarity of signal S2 when pulmonary artery catheter 100 starts to loop. FIG. 8A is a schematic view of the coils on pulmonary artery catheter 100 when pulmonary artery catheter 100 has formed a loop. FIG. 8B is a graph showing an amplitude and polarity of signal S3 when pulmonary artery catheter 100 has formed a loop. FIGS. 6A, 7A, and 8A show catheter 100 (including catheter body 102, first coil 116, and second coil 118), first magnetic field MF1, and second magnetic field MF2. FIG. 6B shows signal S1. FIG. 7B shows signal S2. FIG. 8B shows signal S3.

Catheter 100 has the structure and design as described above in reference to FIGS. 1A-1B. Catheter 100 is connected to detection system 150 as described above in reference to FIGS. 2-5. Third coil 120 and third magnetic field MF3 have been omitted for clarity in FIGS. 6A, 7A, and 8A. In FIGS. 6A-8B, driver/receiver 152 (shown in FIGS. 2-5) sends a signal to and receives a signal from first coil 116 and/or second coil 118. First coil 116 has first magnetic field MF1, and second coil 118 has second magnetic field MF2. First coil 116 and second coil 118 are instrumented such that their amplitude and polarity are known when catheter 100 is not looped or knotted, as shown with the arrows in FIG. 6A. In the embodiment shown in FIG. 6A, first coil 116 and second coil 118 have aligned polarities.

FIG. 6A shows catheter 100 with no loops or knots as it is advanced into the patient. As shown in FIG. 6A, first magnetic field MF1 and second magnetic field MF2 of first coil 116 and second coil 118, respectively, have aligned polarity. Second coil 118 generates second magnetic field MF2 and first coil 116 generates second magnetic field MF1. FIG. 6B shows a graph showing an amplitude and polarity of signal S1 when catheter 100 is not looped or knotted. Signal S1 is a signal received from first coil 116 and/or second coil 118. As shown in FIG. 6B, signal S1 has a small amplitude and positive polarity.

FIG. 7A shows catheter 100 as it starts to loop. A distal end of catheter 100 has turned backwards so first coil 116 has a reversed orientation and is positioned adjacent to second coil 118. As shown in FIG. 7A, the polarity of first magnetic field MF1 of first coil 116 has switched due to the proximity of first coil 116 and second coil 118. FIG. 7B shows a graph showing an amplitude and polarity of signal S2 when catheter 100 has started to loop. Signal S2 is a signal received from first coil 116 and/or second coil 118. As shown in FIG. 7B, signal S2 has a large amplitude and negative polarity.

FIG. 8A shows catheter 100 when a loop has formed. A distal portion of catheter 100 has looped so that first coil 116 has regained its original orientation and is positioned adjacent to second coil 118. As shown in FIG. 8A, the polarity of first magnetic field MF1 and second magnetic field MF2 of first coil 116 and second coil 118, respectively, are realigned because first coil 116 has regained its original orientation. FIG. 8B shows a graph showing an amplitude and polarity of signal S3 when catheter 100 has formed a loop. Signal S3 is a signal received from first coil 116 and/or second coil 118. As shown in FIG. 8B, signal S3 has a large amplitude and positive polarity.

When first coil 116 and second coil 118 are positioned apart, as shown in FIG. 6A, signal S1 has a smaller amplitude. When first coil 116 and second coil 118 get closer together, as shown in FIGS. 7A and 8A, the signal will get stronger due to the proximity of first coil 116 and second coil 118 and the amplitude of the signal will get bigger. This can be seen in signal S2 shown in FIG. 7B and signal S3 shown in FIG. 8B. When the loop starts to form and the orientation of first coil 116 is reversed, as shown in FIG. 7A, signal S2 will be negative due to the differences in polarity of first magnetic field MF1 of first coil 116 and second magnetic field MF2 of second coil 118. When a loop is complete and first coil 116 is reoriented, as shown in FIG. 8A, signal S3 will be positive because the polarity of first magnetic field MF1 and second magnetic field MF2 of first coil 116 and second coil 118, respectively, are again aligned.

Figures 9, 10:
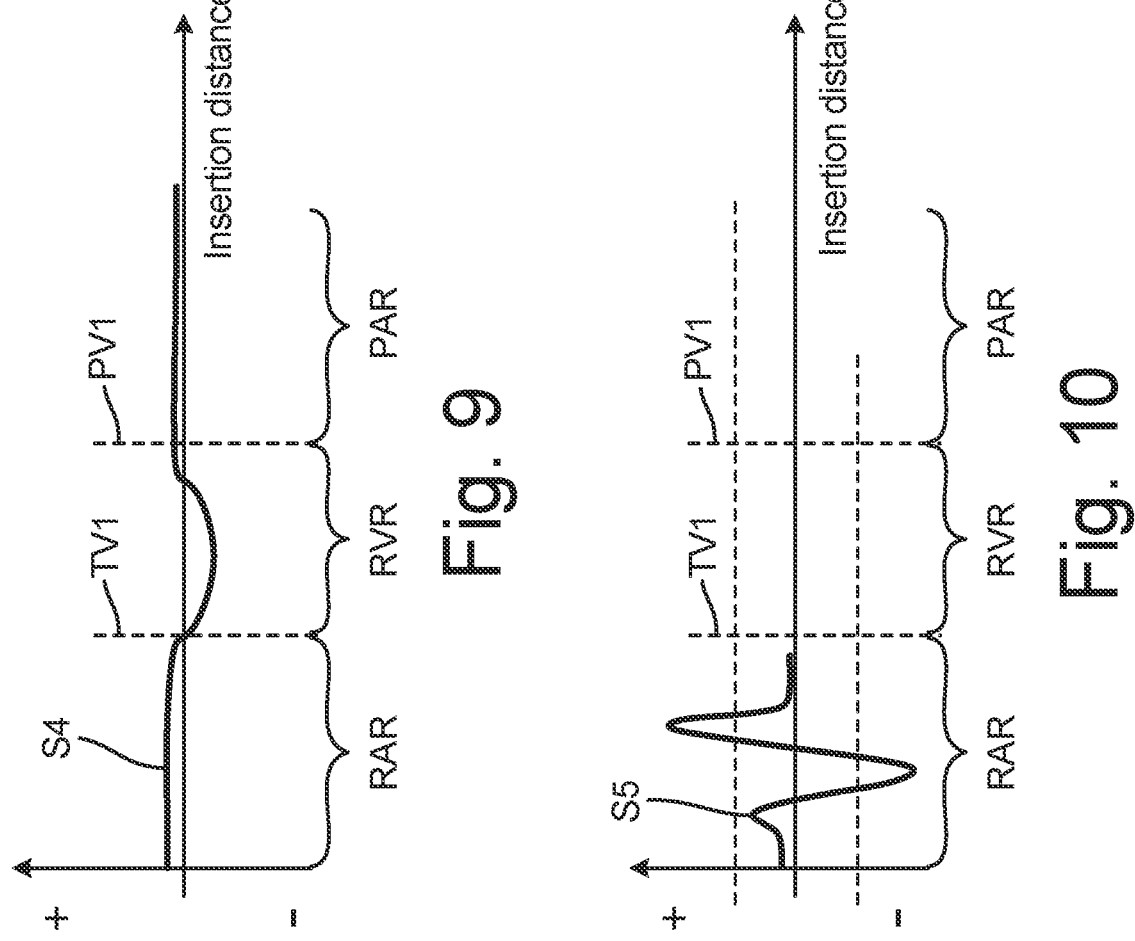
FIG. 9 is a graph showing an amplitude of a signal as the pulmonary artery catheter is advanced from a right atrium to a pulmonary artery.
FIG. 10 is a graph showing an amplitude of a signal as the pulmonary artery catheter forms a loop in the right atrium.

FIG. 9 is a graph showing an amplitude of signal S4 as pulmonary artery catheter 100 is advanced from right atrium RA to pulmonary artery PA. FIG. 10 is a graph showing an amplitude of signal S5 as pulmonary artery catheter 100 forms a loop in right atrium RA. FIGS. 9-10 show region RAR, region RVR, region PAR, dashed line TV1, and dashed line PV1. FIG. 9 also shows signal S4. FIG. 10 also shows signal S5.

FIG. 9 shows changes to signal S4 as catheter 100 (shown in FIGS. 1A-1B) is advanced from right atrium RA (shown in FIG. 1A) to pulmonary artery PA (shown in FIG. 1A). Signal S4 is a signal from first coil 116, second coil 118, and/or third coil 120 (shown in FIGS. 1A-1B) on catheter 100. FIG. 9 shows region RAR, which is when catheter 100 is in right atrium RA, region RVR, which is when catheter 100 is in right ventricle RV (shown in FIG. 1A), and region PAR, which is when catheter 100 is in pulmonary artery PA. FIG. 9 shows dashed line TV1, which represents the point at which catheter 100 passes from right atrium RA through tricuspid valve TV (shown in FIG. 1A) into right ventricle RV, and dashed line PV1, which is the point at which catheter 100 passes from right ventricle RV through pulmonary valve PV (shown in FIG. 1A) into pulmonary artery PA.

Signal S4 has a small, positive amplitude as catheter 100 is advanced through right atrium RA, shown in the graph of FIG. 9 in region RAR. Catheter 100 passes from right atrium RA to right ventricle RV through tricuspid valve TV, shown in the graph of FIG. 9 as dashed line TV1. Signal S4 moves from having a small, positive amplitude to having a small, negative amplitude as catheter 100 passes through tricuspid valve TV. After catheter 100 passes through tricuspid valve TV, signal S4 has a small, negative amplitude as catheter 100 is advanced through right ventricle RV, shown in the graph of FIG. 9 in region RVR. Catheter 100 has to turn in right ventricle RV due to the anatomy of right ventricle RV, which will position first coil 116 adjacent to and in a different orientation from second coil 118, causing the negative amplitude. As catheter 100 approaches pulmonary valve PV, the amplitude of signal S4 will become positive as first coil 116 advances away from second coil 118 and as second coil 118 turns in right ventricle RV. Catheter 100 passes from right ventricle RV to pulmonary artery PA through pulmonary valve PV, shown in the graph of FIG. 9 as dashed line PV1. Signal S4 has a small, positive amplitude as catheter 100 is advanced through and wedged in pulmonary artery PA, shown in the graph of FIG. 9 as region PAR.

FIG. 10 shows changes to signal S5 as catheter 100 is looped in right atrium RA. Signal S5 is a signal from first coil 116, second coil 118, and/or third coil 120 (shown in FIGS. 1A-1B) on catheter 100. FIG. 10 includes region RAR, region RVR, region PAR, dashed line TV1, and dashed line PV1, as discussed above in reference to FIG. 9. As shown in FIG. 10, signal S5 begins with a small, positive amplitude before the amplitude increases slightly as catheter 100 begins to loop. Signal S5 then experiences a large, negative amplitude as catheter 100 begins to form a loop and first coil 116 reorients and gets closer to second coil 118. As catheter 100 loops further, first coil 116 will reorient but remain close to second coil 118, which causes signal S5 to experience a large, positive amplitude. As catheter 100 completes the loop, first coil 116 will move away from second coil 118, which causes the amplitude of signal S5 to decrease.

The amplitude, polarity, and/or trend of the signals from first coil 116, second coil 118, and/or third coil 120 are informative as to the trajectory of pulmonary artery catheter 100. A large amplitude can indicate the likely formation of a loop and/or a knot. Further, an increase in an amplitude and a change in polarity can indicate the likely formation of a loop and/or a knot.

The graphs shown in FIGS. 9 and 10 are examples of graphs of signals that can be displayed on display 156 of detection system 150 (shown in FIGS. 2-5).

Figure 11:
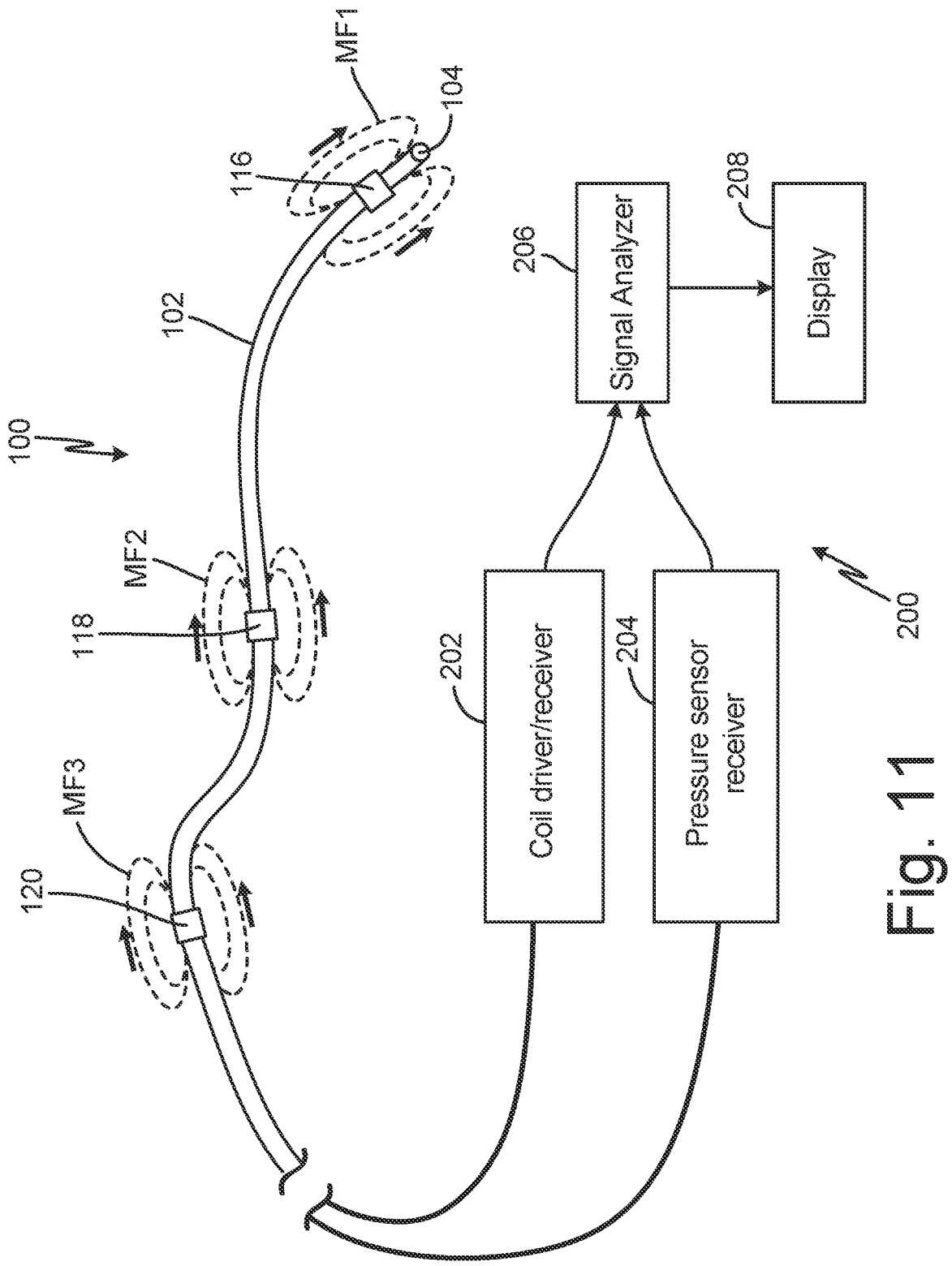
FIG. 11 is a block diagram of a second embodiment of a detection system for detecting looping and knotting of a pulmonary artery catheter.

FIG. 11 is a block diagram of detection system 200 for detecting looping and knotting of pulmonary artery catheter 100. FIG. 11 shows pulmonary artery catheter 100 and detection system 200. Pulmonary artery catheter 100 includes catheter body 102, distal port 104, first coil 116, second coil 118, and third coil 120. Detection system 200 includes coil driver/receiver 202, pressure sensor receiver 204, signal analyzer 206, and display 208. FIG. 11 also shows first magnetic field MF1, second magnetic field MF2, and third magnetic field MF3.

Catheter 100 is schematically shown in FIG. 11, but it has the structure and design as shown in and discussed in reference to FIGS. 1A-1B. Catheter 100 includes catheter body 102 with distal port 104, first coil 116, second coil 118, and third coil 120 positioned on catheter body 102. Detection system 200 will be discussed here as detecting looping and knotting of catheter 100, but detection system 200 can be used with any suitable catheter to prevent looping and knotting of any suitable catheter in alternate embodiments.

Detection system 200 is used to detect looping and knotting of catheter body 102 of catheter 100. Detection system 200 has components similar to detection system 150 discussed above in reference to FIGS. 2-5, including first coil 116, second coil 118, third coil 120, coil driver/receiver 202, signal analyzer 206, and display 208. However, detection system 200 further includes pressure sensor receiver 204.

In the embodiment shown in FIG. 11, coil driver/receiver 202 has the same structure and design of driver/receiver 152 of detection system 150 discussed above in reference to FIGS. 2-5. Coil driver/receiver 202 is connected to catheter 100 with coil connector 139 (shown in FIG. 1B). First coil 116, second coil 118, and third coil 120 are electrically coupled to coil driver/receiver 202 by a wired communication link. Coil driver/receiver 202 is configured to send a signal to and receive a signal from first coil 116, second coil 118, and/or third coil 120. Coil driver/receiver 202 can include a lock-in amplifier, as discussed in reference to FIG. 5, or can be any other suitable driver/receiver. Coil driver/receiver 202 is electrically coupled to signal analyzer 206 by a wired or wireless communication link. The coil signal received in coil driver/receiver 202 from first coil 116, second coil 118, and/or third coil 120 can be communicated to signal analyzer 206 from coil driver/receiver 202.

Driver/receiver 202 drives first coil 116, second coil 118, and/or third coil 120. A magnetic field is created around each of first coil 116, second coil 118, and third coil 120. As shown in FIG. 11, first magnetic field MF1 is formed around first coil 116, second magnetic field MF2 is formed around second coil 118, and third magnetic field MF3 is formed around third coil 120. First magnetic field MF1, second magnetic field MF2, and third magnetic field MF3 are schematically shown in FIG. 11. The polarity of each of first magnetic field MF1, second magnetic field MF2, and third magnetic field MF3 is shown by arrows in FIG. 11.

Detection system 200 also includes pressure sensor receiver 204. Pressure sensor receiver 204 is configured to receive a mixed venous blood sample from distal port 104 and determine a pressure at a distal end of catheter 100 and/or receive a signal from a pressure sensor positioned at a distal end of catheter 100 representative of a pressure at the distal end of catheter 100. Pressure sensor receiver 204 is electrically coupled to signal analyzer 206 by a wired or wireless communication link. Pressure sensor receiver 204 is configured to transmit a pressure signal determined by or received by pressure sensor receiver 204 to signal analyzer 206.

In the embodiment shown in FIG. 11, pressure sensor receiver 204 is connected to catheter 100 using distal port hub 126 (shown in FIG. 1B). Distal port 104 is positioned at a distal end of catheter body 102 and is configured to take a mixed venous blood sample at the distal end of catheter body 102. Distal port hub 126 is fluidly connected to distal port 104 through a lumen extending through catheter body 102 and through extension tube 124A. Pressure sensor receiver 204 is configured to receive the mixed venous blood sample from distal port 104 and to determine a pressure at the distal end of catheter body 102 using the mixed venous blood sample. Pressure sensor receiver 204 can include a pressure sensor or any other suitable electronics that are configured to determine a pressure based on the sample received from distal port 104. In some embodiments, pressure sensor receiver 204 can also include components to determine additional parameters from the mixed venous blood sample taken from distal port 104, such as the assessment of oxygen transport balance and the calculation of oxygen consumption, oxygen utilization coefficient, and intrapulmonary shunt fraction. In an alternate embodiment, catheter 100 can include a pressure sensor positioned at a distal end of catheter 100 that determines a pressure at the distal end of catheter 100 and sends a pressure signal representative of the pressure to pressure sensor receiver 204.

Signal analyzer 206 is configured to analyze both the coil signal from coil driver/receiver 202 and the pressure signal from pressure sensor receiver 204. Signal analyzer 206 is configured to detect changes in first magnetic field MF1, second magnetic field MF2, and/or third magnetic field MF3 from the coil signal and changes in pressure at a distal end of catheter 100 from the pressure signal. Changes occur in first magnetic field MF1, second magnetic field MF2, and/or third magnetic field MF3 and changes occur in an expected pressure at a distal end of catheter 100 when a loop and/or a knot starts to form in catheter 100. Changes in first magnetic field MF1, second magnetic field MF2, and/or third magnetic field MF3 and changes in an expected pressure at the distal end of catheter 100 can be analyzed by signal analyzer 206. Signal analyzer 206 uses an algorithm to compute the likelihood of loop and/or knot formation based on an analysis of the amplitude, polarity, and/or trend of the changes of first magnetic field MF1, second magnetic field MF2, and third magnetic field MF3 of first coil 116, second coil 118, and third coil 120 and the pressure at a distal end of catheter 100.

The expected signals and changes in the expected signals from first coil 116, second coil 118, and/or third coil 120 when a loop or a knot forms are discussed above in reference to FIGS. 6A-10. Additionally, there are expected pressures at a distal end of catheter 100 based on where the distal end of catheter 100 is in a patient's heart (i.e., when it is floating through the right atrium, the right ventricle, and the pulmonary artery, and when it wedges in the pulmonary artery). Changes in the pressure compared to the expected pressure can be determined by signal analyzer 206 and may indicate the formation of a loop and/or a knot in catheter 100.

Signal analyzer 206 is electrically coupled to display 208 by a wired or wireless communication link. After the coil signal and the pressure signal are analyzed by signal analyzer 206, an instruction signal is communicated from signal analyzer 206 to display 208. Display 208 can be configured to display a representation of the coil signal from first coil 116, second coil 118, and/or third coil 120 and the pressure signal from pressure sensor receiver 204, provide an alarm to physician PH regarding looping and/or knotting of catheter 100, and/or instruct physician PH regarding the advancement or removal of catheter 100 when looping and/or knotting of catheter 100 has occurred. For example, the instruction signal that is communicated to display 208 can include an instruction to display an amplitude and a polarity of the coil signal from first coil 116, second coil 118, and/or third coil 120 and a pressure at the distal end of catheter 100 from the pressure signal on display 208. If signal analyzer 206 has detected a change in the coil signal from first coil 116, second coil 118, and/or third coil 120 and/or a change in the pressure signal that indicates the formation of a loop and/or a knot in catheter 100, the instruction signal can include an instruction to display 208 to provide an alarm to physician PH. Further, if signal analyzer 206 has detected a change in the coil signal from first coil 116, second coil 118, and/or third coil 120 and/or a change in the pressure signal that indicates the formation of a loop and/or a knot in catheter 100, the instruction signal can include instructions that are to be provided to physician PH through display 208 regarding the advancement or removal of catheter 100.

Detection system 200 provides a method for real-time, continuous, uninterrupted detection of catheter loop formation and issuance of an alarm if a knot is likely to form. Detection system 200 can determine whether a loop or knot is forming in catheter 100 based on an analysis of coil signals from first coil 116, second coil 118, and/or third coil 120 and pressure signals from catheter 100.

Figures 12, 13A, 13B:
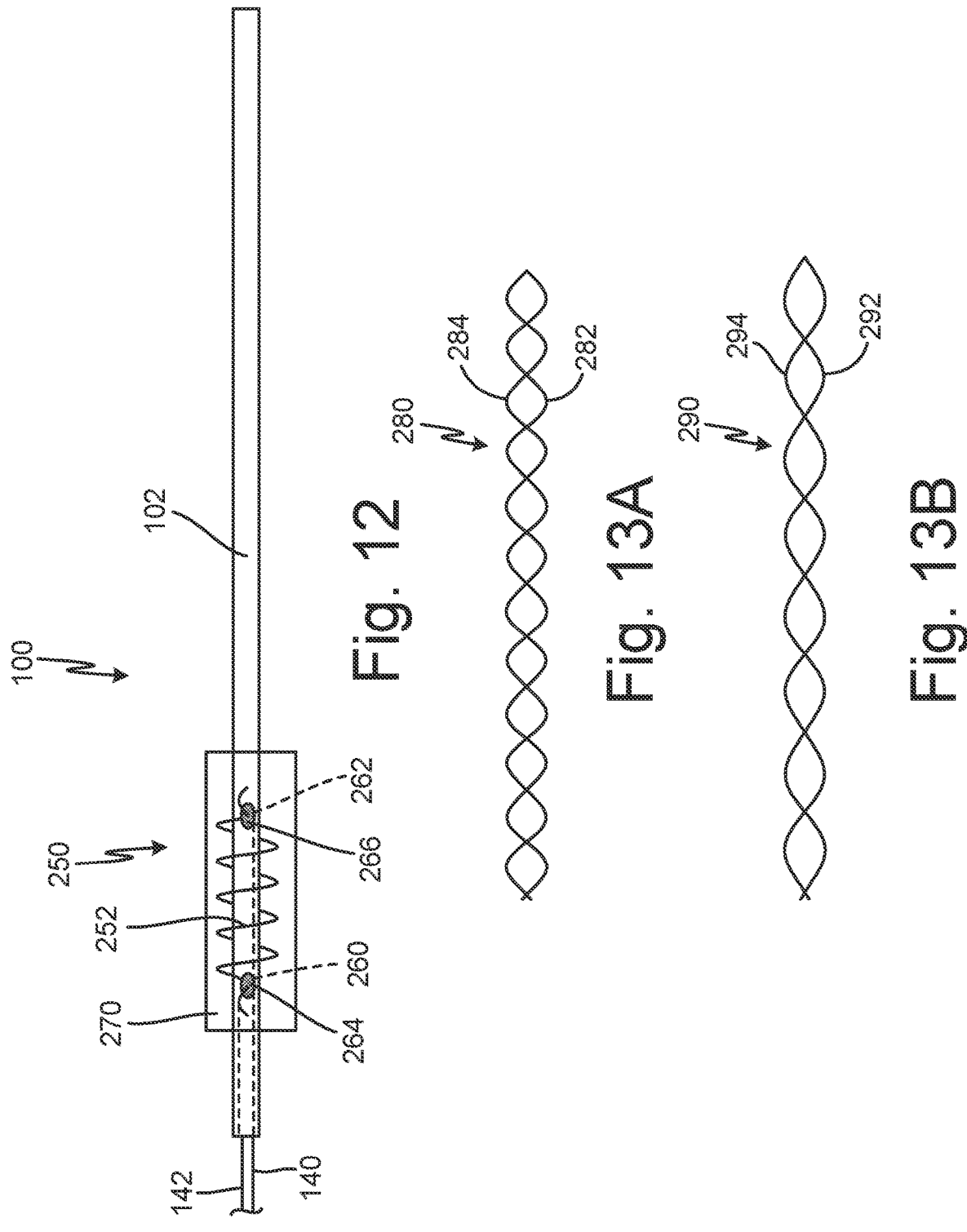
FIG. 12 is a side view of a coil on the pulmonary artery catheter.
FIG. 13A is a side view of a first wire pattern for a coil.
FIG. 13B is a side view of a second wire pattern for a coil.

FIG. 12 is a side view of coil 250 on pulmonary artery catheter 100. Pulmonary artery catheter 100 includes catheter body 102, first wire 140, second wire 142, coil 250 (including wire 252), first aperture 260, second aperture 262, soldering 264, soldering 266, and protective sheath 270.

Catheter 100 includes catheter body 102. First wire 140 and second wire 142 extend through a lumen in catheter body 102 of catheter 100. Coil 250 is positioned on a distal portion of catheter body 102. Coil 250 can be any of first coil 116, second coil 118, or third coil 120 shown in and discussed in reference to FIGS. 1A-1B and 3-5, or any other suitable coil. Coil 250 includes wire 252 that is wound around catheter body 102 of catheter 100. In an alternate embodiment, catheter body 102 of catheter 100 can have a recess for coil 250 to sit in.

Catheter body 102 includes first aperture 260 and second aperture 262 extending through catheter body 102. Wire 252 is wound around catheter body 102 extending from first aperture 260 to second aperture 262. In the embodiment shown in FIG. 12, wire 252 is connected to first wire 140 at first aperture 260 and second wire 142 at second aperture 262. In alternate embodiments of catheter body 102 including additional coils, wire 252 can be connected to first wire 140 at first aperture 260 and second aperture 262, and a second coil can be connected to first wire 140 and second wire 142. Wire 252 is soldered to first wire 140 at first aperture 260 with soldering 264 and to second wire 142 at second aperture 262 with soldering 266. Protective sheath 270 is positioned over wire 252, soldering 264, and soldering 266 and acts as an electrical insulator. Protective sheath 270 is shown as being transparent in FIG. 12 for clarity. Protective sheath 270 can be a heat-shrinkable sheath. Coil 250 can be integrated into catheter 100 using an automated extrusion process.

FIG. 13A is a side view of first wire pattern 280 for a coil. FIG. 13B is a side view of second wire pattern 290 for a coil. FIGS. 13A-13B will be discussed together. First wire pattern 280 includes first wire 282 and second wire 284. Second wire pattern 290 includes first wire 292 and second wire 294.

FIG. 13A shows first wire pattern 280 that includes first wire 282 and second wire 284 that are together twisted around the catheter body of the catheter. First wire 282 and second wire 284 are coupled together. First wire pattern 280 has a small period between first wire 282 and second wire 284. First wire pattern 280 is configured to reduce interference between first wire 282, second wire 284, and their surroundings.

FIG. 13B shows second wire pattern 290 that includes first wire 292 and second wire 294 that are together twisted around the catheter body of the catheter. First wire 292 and second wire 294 are coupled together. Second wire pattern 290 has a larger period between first wire 292 and second wire 294. Second wire pattern 290 is configured to reduce interference between first wire 292, second wire 294, and their surroundings.

First wire pattern 280 and second wire pattern 290 illustrate different twisting patterns and periods. First wire pattern 280 has a smaller period than second wire pattern 290. First wire pattern 280 and second wire pattern 290 are configured to reduce interference between the coil wires.

Discussion of Possible Embodiments

The following are non-exclusive descriptions of possible embodiments of the present invention.

A detection system for detecting a loop and/or a knot in a catheter includes a first coil and a second coil in spaced positions on a catheter body of the catheter. A driver is coupled by a wired communication link to the first coil, wherein the driver is configured to transmit a first signal to the first coil. A receiver is coupled by a wired communication link to the second coil, wherein the receiver is configured to receive a second signal from the second coil indicative of a proximity of the first coil and the second coil. A signal analyzer is coupled by a wired or wireless communication link to the receiver that is configured to receive the second signal from the receiver and determine whether there is a change in the second signal indicative of a formation of the loop and/or the knot in the catheter.

The detection system of the preceding paragraph can optionally include, additionally and/or alternatively, any one or more of the following features, configurations and/or additional components:

Wherein the first coil is a transmit coil and the second coil is a receive coil.

Wherein the first signal from the driver generates a magnetic field around the first coil.

Wherein the second signal is induced into the second coil due to the proximity of the first coil and the second coil.

Wherein the second signal will indicate a change in a magnetic field of the second coil when the loop and/or the knot forms in the catheter.

Wherein the change in the second signal will be a change in an amplitude, a polarity, and/or a trend of the second signal received from the second coil that is indicative of the formation of the loop and/or the knot in the catheter.

Wherein the driver is coupled by the wired communication link to the first coil and the second coil and is configured to transmit the first signal to the first coil and the second coil, wherein the receiver is coupled by the wired communication link to the first coil and the second coil and is configured to receive the second signal from the first coil and the second coil.

Wherein the signal analyzer is configured to determine whether there is a change in impedance of the second signal received from the first coil and the second coil that is indicative of the formation of the loop and/or the knot in the catheter.

Wherein the first coil and the second coil are positioned on a distal portion of the catheter body that is configured to be positioned in a heart and a pulmonary artery of a patient when the catheter is fully positioned in the patient.

Wherein the first coil is positioned adjacent a distal end of the catheter body of the catheter and the second coil is spaced proximal to the first coil.

Wherein the driver and the receiver are a single unit.

Wherein the driver and the receiver are a lock-in amplifier.

Wherein the first signal from the driver is an AC signal.

The detection system further includes a display coupled by a wired or wireless communication link to the signal analyzer, wherein the display is configured to receive an instruction signal from the signal analyzer.

Wherein the instruction signal includes an instruction to display an amplitude and a polarity of the second signal on the display.

Wherein when the signal analyzer has detected a change in the second signal that indicates the formation of the loop and/or the knot in the catheter, the instruction signal includes an instruction to the display to provide an alarm to a physician.

Wherein when the signal analyzer has detected a change in the second signal that indicates the formation of the loop and/or the knot in the catheter, the instruction signal includes an instruction to provide to a physician through the display regarding advancement or removal of the catheter.

The detection system further includes a pressure sensor receiver that is configured to receive or determine a pressure signal from the catheter, wherein the pressure sensor receiver is coupled by a wired or wireless communication link to the signal analyzer.

Wherein the pressure sensor receiver is configured to receive a blood sample from a distal port on a distal end of the catheter and to determine a pressure at the distal end of the catheter using the blood sample.

Wherein the pressure sensor receiver is configured to receive a pressure signal from a pressure sensor positioned at a distal end of the catheter.

Wherein the signal analyzer is configured to analyze the pressure signal from the pressure sensor receiver and the second signal from the receiver to determine whether there is a change in a pressure at a distal end of the catheter and/or a change in the second signal that indicates the formation of the loop and/or the knot in the catheter.

A method for detecting a loop and/or a knot in a catheter includes sending a first signal from a driver to a first coil on the catheter and receiving a second signal from a second coil on a catheter in a receiver. The first coil and the second coil are in spaced positions on a catheter body of the catheter, and the second signal is indicative of a proximity of the first coil and the second coil. The second signal is transmitted from the receiver to a signal analyzer that is coupled to the receiver by a wired or wireless communication link. The signal analyzer determines if there is a change in the second signal that indicates the formation of the loop and/or the knot in the catheter.

The method of the preceding paragraph can optionally include, additionally and/or alternatively, any one or more of the following features, configurations and/or additional components:

The method further includes generating a magnetic field around the first coil with the first signal from the driver.

The method further includes inducing the second signal into the second coil due to the proximity of the first coil and the second coil.

Wherein the signal analyzer will detect a change in a magnetic field around the second coil when the loop and/or the knot forms in the catheter.

Wherein the change in the second signal will be a change in an amplitude, a polarity, and/or a trend of the second signal received from the second coil that is indicative of the formation of the loop and/or the knot in the catheter.

Wherein sending the first signal from the driver to the first coil includes sending the first signal from the driver to the first coil and the second coil, and wherein receiving the second signal from the second coil in the receiver includes receiving the second signal from the first coil and the second coil in the receiver.

Wherein the change in the second signal that indicates the formation of the loop and/or the knot in the catheter is a change in an impedance of the second signal.

The method further includes transmitting an instruction signal from the signal analyzer to a display that is coupled by a wired or wireless communication link to the signal analyzer.

The method further includes displaying an amplitude and a polarity of the second signal on the display based on the instruction signal.

Wherein when the signal analyzer has detected a change in the second signal that indicates the formation of the loop and/or the knot in the catheter, the method further includes providing an alarm to a physician based on the instruction signal.

Wherein when the signal analyzer has detected a change in the second signal that indicates the formation of the loop and/or the knot in the catheter, the method further includes providing an instruction to a physician regarding advancement or removal of the catheter based on the instruction signal.

The method further includes receiving a blood sample in a pressure sensor receiver from a distal port at a distal end of the catheter, determining, in the pressure sensor receiver, a pressure at the distal end of the catheter based on the blood sample, and transmitting a pressure signal representative of the pressure at the distal end of the catheter from the pressure sensor receiver to the signal analyzer.

Wherein the signal analyzer is configured to analyze the pressure signal from the pressure sensor receiver and the second signal from the receiver to determine whether there is a change in the pressure at the distal end of the catheter and/or a change in the second signal indicating the formation of the loop and/or the knot in the catheter.

The method further includes receiving a pressure signal in a pressure sensor receiver from a pressure sensor positioned at a distal end of the catheter that represents a pressure at the distal end of the catheter.

Wherein the signal analyzer is configured to analyze the pressure signal from the pressure sensor receiver and the second signal from the receiver to determine whether there is a change in the pressure at the distal end of the catheter and/or a change in the second signal indicating the formation of the loop and/or the knot in the catheter.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A detection system for detecting a loop and/or a knot in a catheter, the detection system comprising:
   a first coil and a second coil in spaced positions on a catheter body of the catheter;
   a driver coupled by a wired communication link to the first coil, wherein the driver is configured to transmit a first signal to the first coil;
   a receiver coupled by a wired communication link to the second coil, wherein the receiver is configured to receive a second signal from the second coil, wherein the second signal comprises:
   an amplitude indicative of a proximity of the first coil and the second coil; and
   a polarity indicative of a relative orientation of the first coil and the second coil; and
   a signal analyzer coupled by a wired or wireless communication link to the receiver that is configured to receive the second signal from the receiver and determine whether there is a change in the second signal indicative of a formation of the loop and/or the knot in the catheter.

2. The detection system of claim 1, wherein the first coil is a transmit coil and the second coil is a receive coil.

3. The detection system of claim 1, wherein the first signal from the driver generates a magnetic field around the first coil.

4. The detection system of claim 3, wherein the second signal is induced into the second coil due to the proximity of the first coil and the second coil.

5. The detection system of claim 4, wherein the second signal will indicate a change in a magnetic field of the second coil when the loop and/or the knot forms in the catheter.

6. The detection system of claim 5, wherein the change in the second signal is a trend of the second signal received from the second coil that is indicative of the formation of the loop and/or the knot in the catheter.

7. The detection system of claim 1, wherein the driver is coupled by the wired communication link to the first coil and the second coil and is configured to transmit the first signal to the first coil and the second coil, wherein the receiver is coupled by the wired communication link to the first coil and the second coil and is configured to receive the second signal from the first coil and the second coil.

8. The detection system of claim 7, wherein the signal analyzer is configured to determine whether there is a change in impedance of the second signal received from the first coil and the second coil that is indicative of the formation of the loop and/or the knot in the catheter.

9. The detection system of claim 1, wherein the first coil and the second coil are positioned on a distal portion of the catheter body that is configured to be positioned in a heart and a pulmonary artery of a patient when the catheter is fully positioned in the patient.

10. The detection system of claim 1, wherein the first coil is positioned adjacent a distal end of the catheter body of the catheter and the second coil is spaced proximal to the first coil.

11. The detection system of claim 1, wherein the driver and the receiver are a single unit.

12. The detection system of claim 1, wherein the driver and the receiver are a lock-in amplifier.

13. The detection system of claim 1, wherein the first signal from the driver is an AC signal.

14. The detection system of claim 1, further comprising:
a display coupled by a wired or wireless communication link to the signal analyzer, wherein the display is configured to receive an instruction signal from the signal analyzer.

15. The detection system of claim 14, wherein the instruction signal includes an instruction to display an amplitude and a polarity of the second signal on the display.

16. The detection system of claim 14, wherein when the signal analyzer has detected a change in the second signal that indicates the formation of the loop and/or the knot in the catheter, the instruction signal includes an instruction to the display to provide an alarm to a physician.

17. The detection system of claim 14, wherein when the signal analyzer has detected a change in the second signal that indicates the formation of the loop and/or the knot in the catheter, the instruction signal includes an instruction to provide to a physician through the display regarding advancement or removal of the catheter.

18. The detection system of claim 1, further comprising:
a pressure sensor receiver that is configured to receive or determine a pressure signal from the catheter, wherein the pressure sensor receiver is coupled by a wired or wireless communication link to the signal analyzer.

19. The detection system of claim 18, wherein the pressure sensor receiver is configured to receive a blood sample from a distal port on a distal end of the catheter and to determine a pressure at the distal end of the catheter using the blood sample.

20. The detection system of claim 18, wherein the pressure sensor receiver is configured to receive a pressure signal from a pressure sensor positioned at a distal end of the catheter.

21. The detection system of claim 18, wherein the signal analyzer is configured to analyze the pressure signal from the pressure sensor receiver and the second signal from the receiver to determine whether there is a change in a pressure at a distal end of the catheter and/or a change in the second signal that indicates the formation of the loop and/or the knot in the catheter.

* * * * *